(12) United States Patent
Ochiai et al.

(10) Patent No.: US 9,364,492 B2
(45) Date of Patent: Jun. 14, 2016

(54) METHOD FOR GLYCOSYLATION OF FLAVONOID COMPOUNDS

(75) Inventors: Misa Ochiai, Osaka (JP); Harukazu Fukami, Osaka (JP); Masahiro Nakao, Osaka (JP); Akio Noguchi, Osaka (JP)

(73) Assignee: SUNTORY HOLDINGS LIMITED, Osaka (JP)

(*) Notice: Subject to any disclaimer, the term of this patent is extended or adjusted under 35 U.S.C. 154(b) by 673 days.

(21) Appl. No.: 12/523,065

(22) PCT Filed: Jan. 18, 2008

(86) PCT No.: PCT/JP2008/050619
§ 371 (c)(1),
(2), (4) Date: Jul. 14, 2009

(87) PCT Pub. No.: WO2008/088047
PCT Pub. Date: Jul. 24, 2008

(65) Prior Publication Data
US 2010/0256345 A1  Oct. 7, 2010

(30) Foreign Application Priority Data
Jan. 19, 2007  (JP) .................. 2007-010766

(51) Int. Cl.
| C07H 15/203 | (2006.01) |
| C07H 17/065 | (2006.01) |
| A23L 2/52 | (2006.01) |
| A61K 31/7048 | (2006.01) |
| A23L 1/03 | (2006.01) |
| A23L 1/30 | (2006.01) |
| A61K 8/60 | (2006.01) |
| A61K 31/7034 | (2006.01) |
| A61Q 19/00 | (2006.01) |
| C12P 19/14 | (2006.01) |

(52) U.S. Cl.
CPC ............ *A61K 31/7048* (2013.01); *A23L 1/034* (2013.01); *A23L 1/3002* (2013.01); *A23L 2/52* (2013.01); *A61K 8/602* (2013.01); *A61K 31/7034* (2013.01); *A61Q 19/00* (2013.01); *C07H 15/203* (2013.01); *C07H 17/065* (2013.01); *C12P 19/14* (2013.01); *A23V 2002/00* (2013.01)

(58) Field of Classification Search
None
See application file for complete search history.

(56) References Cited

U.S. PATENT DOCUMENTS 5,834,251 A * 11/1998 Maras et al. ................. 435/71.1
2003/0082751 A1  5/2003 Okada et al.

FOREIGN PATENT DOCUMENTS

| JP | 5-176786 | 7/1993 |
| JP | 6-277087 | 10/1994 |
| JP | 6-284897 | 10/1994 |
| JP | 7-10897 | 1/1995 |
| JP | 7-179489 | 7/1995 |
| JP | 08217674 | * 8/1996 |
| JP | 8-298930 | 11/1996 |
| JP | 9-3089 | 1/1997 |
| JP | 2001-46096 | 2/2001 |
| JP | 2003-171328 | 6/2003 |
| WO | 01/73106 | 10/2001 |

OTHER PUBLICATIONS

Moon et al. J. Agric. Food Chem. (2006) 54(4): 1230-1237.*
Moon et al., Journal of Agric. Food Chem., 2006, 54(4), 1230-37.*
Kashiwada et al, Chemical and Pharmaceutical Bulletin, 1986, 34(8), pp. 3208-3222.*
Moon et al., Journal of Agric. Food Chem., 2006, 54(4), 1230-1237.*
English Translation of JP07-179489—Jul. 18, 1995.*
English Translation of JP08-217674—Aug. 27, 1996.*
Gao C., et al., Novel enzymatic . . . their esters., Biotechnology and bioengineering, 2001, 71(3), pp. 235-243.
Meulenbeld G., et al., Enhanced (+)-Catechin . . . Fructose Removal., Appl Environ Microbiol. Sep. 1999; 65(9): 4141-4147.
Japanese Office Action issued with respect to patent family member JP 2007-010766, mailed Oct. 1, 2012.
Nanjo et al., "Scavenging Effects of Tea Catechins and Their Derivatives on 1,1-Diphenyl-2-picrylhydrazyl Radical" *Free Radical Biology & Medicine*, vol. 21, No. 6, p. 895-902 (1996).
Nanjo et al., "Radical Scavenging Activity of Tea Catechins and Their Related Compounds" *Biosci. Biotechnol. Biochem.*, vol. 63, No. 9, p. 1621-1623 (1999).
Pachaco-Chavez et al., "Production of α-Amylase and Glucoamylase by a New Isolate of *Trichoderma* sp. Using Sorghum Starch as a Carbon Source" *Eng. Life Sci.*, vol. 4, No. 4, p. 369-372 (2004).
Extended European Search Report issued with respect to European Patent Application No. 14150736.8, mailed Apr. 7, 2014.
Pacheco Chavez et al., "Production of α-Amylase and Glucoamylase from Different Starches by a New *Trichoderma* sp. Isolate" *Annals of Microbiology* 54(2):169-180, 2004.
Schellart et al., "Starch Degradation of the Mould *Trichoderma viride*, I. The Mechanism of Starch Degradation" *Antonie van Leeuwenhoek* 42:229-238, 1976.
Extended European Search Report for patent family member European Patent App. No. 08703469.0, dated May 31, 2013.

* cited by examiner

*Primary Examiner* — Traviss C McIntosh, III
(74) *Attorney, Agent, or Firm* — Greenblum & Bernstein, P.L.C.

(57) ABSTRACT

The present invention provides a method for preparing a glycoside of a flavonoid compound, which comprises the step of treating flavonoid and a glycosyl donor with an enzymatic agent having glycosylation activity and being derived from the genus *Trichoderma* (preferably *Trichoderma viride* or *Trichoderma reesei*). Such a flavonoid compound includes a catechin compound or a methylated derivative thereof, and the glycosyl donor includes a carbohydrate containing a maltotriose residue (preferably maltotriose, maltotetraose, maltopentaose, maltohexaose, maltoheptaose, dextrin, γ-cyclodextrin or soluble starch). Glycosides obtained by the present invention have higher water solubility, improved taste, and increased stability. The present invention also provides novel glycosides of catechin compounds, which are obtained by the method of the present invention.

8 Claims, 8 Drawing Sheets

Figure 3

```
                                                                                                                                                                 150
EAA63356   ----------------------------------------------------------------------------------------------------------------------------------------------------------
EAA71544   ----------------------------------------------------------------------------------------------------------------------------------------------------------
EAA48146   ----------------------------------------------------------------------------------------------------------------------------------------------------------
EAA47529   MANKILVAYIFADFLFVLMGALMLGFSIVVGNVRDEVPTEGNQAARNLLYQKFPLTAGIVNAIFIFITFLLTIPALSTPARGWLKMSGYLVVVNALFSLVIGLFLWIMTLKTRDDLFPIWVQQTPQVQSLMEVSFKCCGYNSTAPAFVT 151                                                                                                                                                   300
EAA63356   -----------------------------------------------MKLASTLAGLLEPLISFVSAADVDAWK------------------SRNIYFALTDRVARGSDDTGGDACDDLSTYCGGTFKGLEGKLDYIKGMGFDAIWITPVVANHDGGYHGYWAKDL
EAA71544   -----------------------------------------------MKLLQLAALVASISPFASAADANAWK------------------SRNIYFALTDRVARSDSDSGGNAGSNLGNYCGGTFKGLEAKLDYIKGMGFDAIWITPVVENTDGGYHGYWAKDL
EAA48146   -----------------------------------------------MFFFKVLVAFELQIVTVYAADTAAWK------------------SRSIYFALTDRVARGSNDTGGASEGNLSKYCGGTFKGLESKLDYIKNLGFDSIWINPVVSNKADGYHGYWAQDL
EAA47529   NQVCPSPAASALMRGCATPITSFANVFVDNIFTGVFGMCGIDGLEVIATACLLKDRKEQERFRHIDQKTGPMSTLPCQTSVVRQADRIARNESDSGGNSCSDLCQYCCGTFKGLQSKLDYIRGMGFDAIWISPVVENHKGGYHGYWAKDL 301                                                                                                                                                   450
EAA63356   YSINENYGTADDLKSLVSAAHEKGIYIMADVVANHWGSP-ISDNQPESLSQESAYHSACTIDYSSQESIETCRIADDLPDVNTESEEIRTLFKEWITWLVKEYEFDGLRIDTVKHVEKDFWSDFSSAAGVYTIGEVFDGDPDYLAGYANT
EAA71544   YEVNAKYGTKDDLKSLVKTAHSKNIYYMADVVANHWGKG-IQDHRFEPLNQQSSYHSPCAIDYNMQNSIEQCEIAD-LPDLNTGSETVKKVLNDWISWLVTEYSFDGIRIDTVKHVEKSFWPDFQKAAGVYAIGEVWDGSPDYLAGYSKV
EAA48146   YAINSNYGSAADLKSLVNTAHSKGIYMVDVVANHMGPGSISDNRPAPLINQNSSYHSQCTIDNSNQSSVENCWVAN-LPDINTQSSGIRQLLNTWVSWLVKEYSFDGVRIDTVKHVEKSFWPGFVKSIGAYAIGEVFDGNPSFMAGYANL
EAA47529   YAINSKYGTADDLKSLIKAAHDKGFLLMVDVVANHMGNGPISENKPAPLNQESSYHPECKIDYSNQQSVERCRLGN-LPDLNTEDPKIRTLLTDWIKWIVSEFKVDGLRIDTVKHVEKGFWPGFAWASGVYTLGEVYSEDVDYLAGYDKT 451                                                                                                                                                   600
EAA63356   MDGLLNYAVYPVNNFYQQAGSAQDIVDMHDKIDSSFPDPSALGTFIDNHDNARWLSNKDDKSLIEKNALAYVLLARGIPIVYYGTEQGYAGGNDPENREDLWRSNFDTDADLEYKAISLLSAARSAAGGLGDNDHVHLVAESAYAWSRAE
EAA71544   MPGLLNYAIIYYPMNRFYQQKGDFSAVVDMYNEISQKFDDPTVLGTFIDNHDNPRWLSQKNDKALLKNALAYVFLSRGIPIVYFSGTEQGYAGGNDPANREDLWRSSFKTDSDLYQTISKLGKARSAVGGLAGNDQKFLKSMDSALIWSRAN
EAA48146   MPGLLNYAVYYPMNRFYQQGNSPQELVNMIDNITASFPDPAALGTFLDNHDNPRWLNQTNDQTLLQNALAFVLSRGIPIVYFGTEQGLVGGDDPANREDLWRSGYKTDTTLHGAVAKLNAARKAAGGLDGNDHTHLYVTNDTYAWSRAG
EAA47529   MGGFFNFPVYKSLGRYLQGGQSPQGLVDNHDKITRKFSDPTTLANFLDSHDDPRWLSKNRDAALLKNALAYVLLARGIPVVYYGTEQFSGGADPWNREDLWRARYRTDGDLYRAISRLSGVRAGAGGLPADDQIHLLVNKNSYAFSRDG 601                                                                                                                                                   750
EAA63356   GKLVWVTFSNSGSGSENEICFDSKTPNGSWENIFGEGT-ISADDSGGQICVSITNGEPAVLVAQS-------------------------------------------------------------------------------------------
EAA71544   NDLIVVTMNRGQGFSGQYCFENTGANNKTWERVLCQGT-VKSDGSCGLCVSYTNGEPVLVAAN---------------------------------------------------------------------------------------------
EAA48146   ADLVVLTTNAGRCSHAQHCFNTTRANGRWADVYCGSGAYVFSDKTGRACVKLANGQPVVLLALANSTTGDKPPTLPAPITWYNSTSPPDSANGSNVCPPAVAVSFTVRVATAPGDTIKMVGNTAQLGSWDAAKAPSLSASGYNSTNMAW
EAA47529   GGVVVLTTNRGSGFWGQGEFDTRGVTATWEDKFGSGT-YTSDESGKVCVCVQVKNGEPVKRKK---------------------------------------------------------------------------------------------

751                         801
EAA63356   --------------------------------
EAA71544   --------------------------------
EAA48146   SITLPMAPGRTVQKFVQKFVYSRSGGTTWESDPNRFYTPPVSQATADVSNIWR
EAA47529   --------------------------------
```

```
1     ATGAAGCTTC GATCCGCCGT CCCGCTGCTG TTGCAGCTTT CTCTCCCGGC CGTCCTTGGC GCCGACACGG CAGACTGGAG GTCTCGTACC ATCTACTTTG CCCTGACAGA CCGAATTGCT
      M K L R  S A V  P L L  L Q L S  L P A  V L G  A D T A  D W R  S R T  I Y F A  L T D  R I A

121   CGCAGCTCAA GCGACACGGG AGGCTCTGCG TGTACAAATC TGAATGACTA CTGTGGTGGC ACGTTCCAGG GCTTGGAGAG CAAGCTGGAC TACATCAAGG GCATGGGATT TGATGCCATC
      R S S S  D T G  G S A  C T N L  N D Y  C G G  T F Q G  L E S  K L D  Y I K G  M G F  D A I

241   TGGATCAACC CCGTCGTAAC CAACAGTGAT TTCGGCTTCC ATGGCTACTG GGCACTGGAT CTAAACACTA TCAATTCTCA CTATGGCACT GCGGATGATT TAAAGAGTCT CGTTGATGCT
      W I N P  V V T  N S D  F G F H  G Y W  A L D  L N T I  N S H  Y G T  A D D L  K S L  V D A

361   GCACATGGCA AGGGCTTCTA CATGATGGTC GACGTTGTAG CCAACCACAT GGGAAACGCA AACATCACAG ACGACTCCCC CTCCCCTCTG AACCAACAAT CCTACATACCA CACAAAATGT
      A H G K  G F Y  M M V  D V V A  N H M  G N A  N I T D  D S P  S P L  N Q Q S  S Y H  T K C

481   GACATTGACT TCAACAACCA GACCAGCGTC GAAAACTGTT GGCTTGCTGG CCTCCCAGAC GTTGACACCC AGGACCCTAC CATCAGGAGC CTCTACCAGG ACTGGGTGTC CAACCTGGTA
      D I D F  N N Q  T S V  E N C W  L A G  L P D  V D T Q  D P T  I R S  L Y Q D  W V S  N L V

601   TCTACATACG GCTTCGACGG CGTCCGCATC GACACCGTCA GGCACGTCGA GCAGGACTAC TGGCCCGGCT TCGTCAATGC CAGCGGCGTG TACTGCATCG GCGAAGTCTT CAACGGAGAC
      S T Y G  F D G  V R I  D T V R  H V E  Q D Y  W P G F  V N A  S G V  Y C I G  E V F  N G D

721   CCAGACTTTA TGCAGCCCTA CCAATCGCTC ATGCCCGGCC TCCTCAACTA CGCCATCTTC TACCCCCTCA ACGCCTTTTA TCAGCAGACG GGCTCCTCCC AAGCCCTGGT CGACATGCAT
      P D F M  Q P Y  Q S L  M P G L  L N Y  A I F  Y P L N  A F Y  Q Q T  G S S Q  A L V  D M H

841   GACCGTCTCA GCTCGTTCCC AGACCCGACG GCGCTGGGCA CCTTTGTCGA TAACCACGAC AACCCCCGCT TCCTCAGCGT CAAGAACGAC ACGTCTCTCT TCAAGAATGC CCTGACCTAC
      D R L S  S F P  D P T  A L G T  F V D  N H D  N P R F  L S V  K N D  T S L F  K N A  L T Y

961   ACCATTCTCG GCCGAGGCAT CCCCATTGTC TACTACGGCT CCGAGCAAGC CTTTTCGGGA AGCAACGACC CCGCCAACAG AGAGGACCTC TGGCGCAGCG GCTACAACAC CGAGACGGAC
      T I L G  R G I  P I V  Y Y G S  E Q A  F S G  S N D P  A N R  E D L  W R S G  Y N T  E T D

1081  ATGTACAATG CCATCTCCAA GCTCACCTTT GCCAAGCACA CGGCCGGCGG CCTCGCCGAC AACGACCACA AGCACCTGTA CGTCGAGCCC ACGGCATACG CCTGGAGCCG CGGCGGCGGC
      M Y N A  I S K  L T F  A K H T  A G G  L A D  N D H K  H L Y  V E P  T A Y A  W S R  A G G

1201  AAGCTGGTGG CCTTTACCAC CAACAGCGGC GGCGGCAGCT CGGCCCAGTT CTGCTTCGGC ACGCAGGTCC CCAACGGGAG CTGGACGAAT GTGTTTGATG GCGGCAATGG CCCGACGTAC
      K L V A  F T T  N S G  G G S S  A Q F  C F G  T Q V P  N G S  W T N  V F D G  G N G  P T Y

1321  ACTGCTGATG GCAATGGACA GCTCTGCTTG ACCACGACGA ATGGTGAGCC GATTGTGCTG CTGTCTTCAT AA
      T A D G  N G Q  L C L  T T T N  G E P  I V L  L S S
```

Figure 6

```
              1                                                                                                      100
       TRa2   -MKLRSAVPLLLQLSLPAVLGADTADWRSRTIYFALTDRIARSSSDTGGSACTNLNDYCGGTFQGLESKLDYIKGMGFDAIWINPVVTNS------DFGF
    BAA00336  MMVAWWSLFEYGLQVAAPALAATPADWRSQSIYFLLTDRFARTDGSTTATCNTADQKYCGGTWQGIIDKLDYIQGMGFTAIWITPVTAQLPQTTAYGDAY 101                                                                                                    200
       TRa2   HGYWALDLNTINSHYGTADDLKSLVDAAHGKGFYMMVDVVANHMGNANITDDSPS-----PLNQQSSYHTKCDID-FNNQTSVENCWLAG----LPDVDTQ
    BAA00336  HGYWQQDIYSLNENYGTADDLKALSSALHERGMYLMVDVVANHMGYDGAGSSVDYSVFKPFSSQDYFHPFCFIQNYEDQTQVEYCWLGDNTVSLLDLDTT 201                                                                                                    300
       TRa2   DPTIRSLYQDWVSNLVSTYGFDGVRIDTVRHVEQDYWPGFVNASGVYCIGEVFNGDPDFMQPYQSLMPGLLNYAIFYPLN-AFYQQTGSSQALVDMHDRL
    BAA00336  KDVVKNEWYDHVGSLVSNYSIDGLRIDTVKHVQKDFWPGYNKAAGVYCIGEVLDVDPAYTCPYQNVMDGVLNYPIYYPLLNAFKSTSGSMDDLYNMINTV
                                        *                            *

301                                                                                                    400
       TRa2   SS-FPDPTALGTFVDNHDNPRFLSVKNDTSLFKNALTYTILGRGIPIVYYGSEQAFSGSNDPANREDLWRSGYNTETDMYNAISKLTFAKHTAG----GL
    BAA00336  KSDCPDSTLLGTFVENHDNPRFASYTNDIALAKNVAAFIILNDGIPIIYAGQEQHYAGGNDPANREATWLSGYPTDSELYKLIASANAIRNYAISKDTGF
                    *

401                                                                                                    499
       TRa2   ADNDHKHLYVEPTAYAWSR--AGGKLVAFTTNSGGGSSAQFCFGTQVPNGSWTNVFDGGNGPTYTADGNGQLCLTTTNGEPIVLLSS-----------
    BAA00336  VTYKNWPIYKDDTTIAMRKGTDGSQIVTILSNKGASGDSYTLSLSGAGYTAGQQLTEVIGCTTVTVGSDGNVPVPMAGGLPRVLYPTEKLAGSKICSSS
```

METHOD FOR GLYCOSYLATION OF FLAVONOID COMPOUNDS

TECHNICAL FIELD

The present invention relates to glycosylation of flavonoid compounds. Glycosides of flavonoid compounds obtained by the present invention can be used for food, pharmaceutical and cosmetic purposes.

BACKGROUND ART

Proanthocyanidin (grape seed extract) has been studied for its usefulness as a therapeutic agent for blood vessels, and one of the reasons for recent progress in these studies is that the target substance can serve as a marker for tracing in vivo absorption and metabolism because it is stable against heat and acids, highly soluble in water and highly absorbable in the body. In contrast, polyphenol compounds such as catechin are often difficult to dissolve in water, and also involve a problem in that they are less absorbable in the body.

Attempts have been made to develop a technique for glycosylation of catechin and other compounds, with the aim of improving their solubility in water and increasing their stability.

By way of example, Patent Document 1 discloses α-glucosidase with a molecular weight of about 57,000, which was collected from a culture solution of *Xanthomonas campestris* WU-9701. This enzyme uses maltose or the like as a donor (does not use maltotriose, cyclodextrin or starch as a donor) and transfers glucose to a specific acceptor to synthesize a glycoside. In this document, compounds listed as acceptors are those having an alcoholic hydroxyl group (e.g., menthol, ethanol, 1-propanol, 1-butanol, 2-butanol, isobutyl alcohol, 1-amyl alcohol, 2-amyl alcohol, 5-nonyl alcohol), as well as those having a phenolic hydroxyl group (e.g., capsaicin, dihydrocapsaicin, nonylic acid vanillylamide, catechin, epicatechin, vanillin, hydroquinone, catechol, resorcinol, 3,4-dimethoxyphenol). Moreover, glycosides whose production was actually confirmed are monoglucosides only.

Patent Document 2 discloses a method in which a mixture of a catechin compound and glucose-1-phosphate or sucrose is treated with sucrose phosphorylase to prepare a glycoside of the catechin compound. The sources of sucrose phosphorylase listed therein are *Leuconostoc mesenteroides*, *Pseudomonas saccharophila*, *Pseudomonas putrefaciens*, *Clostridium pasteurianum*, *Acetobacter xylinum*, and *Pullularia pullulans*. Likewise, catechin compounds listed as acceptors are (+)-catechin, (−)-epicatechin, (−)-epicatechin 3-O-gallate, (−)-epigallocatechin and (−)-epigallocatechin 3-O-gallate, but it is only (+)-catechin that was actually used as an acceptor to prepare (+)-catechin 3'-O-α-D-glucopyranoside in the Example section.

Patent Document 3 discloses epigallocatechin 3-O-gallate derivatives, in which a glucose residue or a maltooligosaccharide residue with a polymerization degree of 2 to 8 is attached to at least one of the 5-, 7-, 3'-, 4'-, 5'-, 3"-, 4"- and 5"-positions. As in the case of Patent Document 2, the Example section of Patent Document 3 actually discloses only a case where a mixture of (−)-epigallocatechin gallate and glucose-1-phosphate or sucrose was treated with sucrose phosphorylase to prepare 4'-O-α-D-glucopyranosyl(−)-epigallocatechin gallate and 4',4"-O-α-D-di-glucopyranosyl(−)-epigallocatechin gallate.

Patent Document 4 discloses tea extracts or tea beverages whose astringent taste is reduced by glycosylation of polyphenols contained therein. To reduce the astringent taste of tea extracts or tea beverages, this document describes detailed procedures in which tea extracts or tea beverages are supplemented with dextrin, cyclodextrin, starch or a mixture thereof, and then treated with cyclomaltodextrin glucanotransferase. In the Example section, it is shown that a green tea extract and α-cyclodextrin were treated with cyclomaltodextrin glucanotransferase derived from *Bacillus stearothermophilus* to give a reaction product with reduced astringent taste, which in turn indicates that polyphenols such as epigallocatechin 3-O-gallate and epicatechin were glycosylated. However, this document fails to show the detailed structure of the reaction product.

Patent Document 5 discloses glycosides of catechin compounds in which glycosylation occurs at the 3'-position, at the 3'- and 5-positions, or at the 3'- and 7-positions. For this purpose, this document describes detailed procedures in which a catechin compound and dextrin, cyclodextrin, starch or a mixture thereof are treated with cyclomaltodextrin glucanotransferase derived from *Bacillus stearothermophilus*, as in the case of Patent Document 4. Further, in the examples using dextrin as a glycosyl donor in the above procedures, some of the resulting glycosides of (−)-epigallocatechin, (−)-epigallocatechin 3-O-gallate and (−)-epicatechin 3-O-gallate are considered to have 6 to 8 glucose residues on average per molecule of each polyphenol, as determined from their molar absorption coefficients. Moreover, it is confirmed that upon treatment with glucoamylase derived from *Rhizopus niveus*, the glycosides obtained by the above procedures generated 3',7-di-O-α-D-glucopyranosyl(−)-epigallocatechin, 3',5-di-O-α-D-glucopyranosyl(−)-epigallocatechin, 3'-O-α-D-glucopyranosyl(−)-epigallocatechin, 3',7-di-O-α-D-glucopyranosyl(−)-epigallocatechin 3-O-gallate, 3'-O-α-D-glucopyranosyl(−)-epigallocatechin 3-O-gallate, 3'-O-α-D-glucopyranosyl(−)-gallocatechin and 3'-O-α-D-glucopyranosyl(−)-epicatechin 3-O-gallate.

As to effects provided by catechin glycosides, Non-patent Document 1 describes reduced astringent taste, increased water-solubility, improved stability and inhibited tyrosinase, while Non-patent Document 2 describes suppressed mutagenicity.

Patent Document 1: JP 2001-46096 A
Patent Document 2: JP 05-176786 A (Japanese Patent No. 3024848)
Patent Document 3: JP 07-10897 A (Japanese Patent No. 3071610)
Patent Document 4: JP 08-298930 A (Japanese Patent No. 3579496)
Patent Document 5: JP 09-3089 A (Japanese Patent No. 3712285)
Non-patent Document 1: Biosci. Biotech. Biochem., 57 (10), 1666-1669 (1993)
Non-patent Document 2: Biosci. Biotech. Biochem., 57 (10), 1290-1293 (1993)

DISCLOSURE OF THE INVENTION

Problems to be Solved by the Invention

These glycosylation techniques cannot be regarded as sufficient in terms of properties of the enzymes used therein, including glycosyl donor specificity, specificity to compounds which can be glycosylated, glycosylation efficiency, etc. Thus, there has been a demand for a preparation technique which allows glycosylation of a wider variety of flavonoid compounds, and for flavonoid glycosides.

Means for Solving the Problems

The inventors of the present invention have made extensive and intensive efforts to develop a glycosylation technique for flavonoid compounds including catechin. As a result, the inventors have found that various enzymatic agents derived from the genus *Trichoderma* have glycosylation activity on flavonoid, thereby completing the present invention.

The present invention provides a method for preparing a glycoside of a flavonoid compound, which comprises the step of treating the flavonoid compound and a glycosyl donor with an enzymatic agent having glycosylation activity and being derived from the genus *Trichoderma*.

[Flavonoid Compounds]

As used herein, the term "flavonoid compound" is intended to include both flavonoid and esculetin, unless otherwise specified.

As used herein, the term "flavonoid" is intended to mean a catechin compound (flavanol), flavanone, flavone, flavonol, flavanonol, isoflavone, anthocyan or chalcone, as well as a methylated derivative thereof, unless otherwise specified. Flavonoid includes naringenin, quercetin, daidzein, genistein and kaempferol. Flavonoid available for use in the present invention may be of natural or synthetic origin.

As used herein, the term "catechin compound" is used in a broad sense to mean a polyoxy derivative of 3-oxyflavan, unless otherwise specified. This includes catechin, gallocatechin and 3-galloyl derivatives thereof, as well as optical isomers ((+)-, (−)-, (+)-epi- and (−)-epi-isomers) and racemates thereof. Specific examples include catechin, gallocatechin (GC), catechin gallate (catechin-3-O-gallate; CG), gallocatechin gallate (gallocatechin-3-O-gallate; GCG), epicatechin (EC), epigallocatechin (EGC), epicatechin gallate (epicatechin-3-O-gallate; ECG) and epigallocatechin gallate (epigallocatechin-3-O-gallate; EGCG), as well as optical isomers thereof. Methylated derivatives of catechin compounds refer to derivatives of the above catechin compounds, in which H in at least one OH group is replaced by methyl. Examples of methylated derivatives of catechin compounds include those having methyl in place of H in the OH group located at any of the 3'-, 4'-, 3"- and 4"-positions of epicatechin, epigallocatechin, epicatechin gallate or epigallocatechin gallate. Catechin compounds and their methylated derivatives available for use in the present invention may be of natural or synthetic origin. Examples of natural origin include tea extracts, concentrated and purified products thereof (e.g., green tea extracts such as Teavigo (DSM Nutrition Japan), Polyphenon (Mitsui Norin Co., Ltd., Japan) and Sunphenon (Taiyo Kagaku Co., Ltd., Japan)), as well as extracts of a tea cultivar "Benifuki."

In the present invention, flavonoid compounds may be used either alone or in combination.

[Enzymatic Agents]

The present invention uses an enzymatic agent having glycosylation activity and being derived from the genus *Trichoderma*. The genus *Trichoderma* includes *Trichoderma viride*, *Trichoderma reesei*, *Trichoderma saturnisporum*, *Trichoderma ghanense*, *Trichoderma koningii*, *Trichoderma hamatum*, *Trichoderma harzianum* and *Trichoderma polysporum*.

As used herein, the term "enzymatic agent" may be used to mean either a single enzyme or a mixture of multiple enzymes, unless otherwise specified. Although such an enzymatic agent comprises at least an enzyme having glycosylation activity, it may further comprise other glycosidase enzymes, such as those used as cellulase or glucanase (e.g., β-1,3-glucanase). Moreover, the enzymatic agent of the present invention may comprise an appropriate additive, in addition to the enzyme component. Examples include excipients, binders, disintegrating agents, stabilizers, buffers and preservatives.

Enzymatic agents available for use in the present invention have at least glycosylation activity (transglycosylation).

As used herein, the term "glycosylation activity" is intended to mean having the ability to transfer a sugar residue to a flavonoid compound. To confirm whether an enzyme has the ability to transfer a sugar residue to a flavonoid compound, unless otherwise specified, a mixture of flavonoid (e.g., catechin) and an appropriate glycosyl donor (e.g., dextrin) may be contacted with the target enzyme and reacted for a sufficient period of time, followed by analysis of the reaction solution through high performance liquid chromatography (HPLC) or other techniques, for example as shown in the Example section described later.

The enzymatic agent of the present invention may have not only glycosylation activity, but also an additional activity, such as dextrinase activity. As used herein, the term "dextrinase" is intended to mean an enzyme capable of hydrolyzing carbohydrates containing α-glucoside linkages (e.g., starch, dextrin), unless otherwise specified. Dextrinase is a kind of amylase. To determine whether a target has dextrinase activity, a commercially available dextrin (e.g., starch hydrolyzed with an acid, heat or an enzyme to have an average molecular weight of about 3,500) may be treated with the target under appropriate conditions to examine whether the dextrin is hydrolyzed. Those skilled in the art would design appropriate conditions for reaction with a target and procedures for determining whether dextrin is hydrolyzed.

In the present invention, enzymatic agents which can be preferred for use are those having glycosylation activity and being derived from the genus *Trichoderma*. In the present invention, enzymatic agents which may be effective for use are those derived from *Trichoderma viride* and used as cellulase or β-1,3-glucanase. According to the studies of the inventors, it has been found that various enzymatic agents derived from the genus *Trichoderma*, such as those used as cellulase or glucanase (e.g., β-1,3-glucanase), have glycosylation activity, and that such enzymatic agents can be effective for use in glycosylation of flavonoid compounds. For example, in the present invention, it is possible to use commercially available enzymatic agents, such as those listed in Table 1 of Example 2 described later.

Alternatively, for use as enzymatic agents in the present invention, those skilled in the art can isolate and purify glycosyltransferases from cultures of species belonging to the genus *Trichoderma* (e.g., *Trichoderma viride*, *Trichoderma reesei*, *Trichoderma saturnisporum*, *Trichoderma ghanense*, *Trichoderma koningii*, *Trichoderma hamatum*, *Trichoderma harzianum* or *Trichoderma polysporum*) by using conventional techniques. Among such glycosyltransferases, particularly preferred is a glycosyltransferase obtained from the culture supernatant of *Trichoderma viride* strain IAM5141 (herein also referred to as "TRa2") or a homolog thereof, i.e., a protein comprising (i), (j) or (k) shown below (preferably a protein consisting of (i), (j) or (k) shown below):

(i) a protein which consists of the amino acid sequence shown in SEQ ID NO: 10;

(j) a protein which consists of an amino acid sequence comprising substitution, deletion, insertion and/or addition of one or several amino acids in the amino acid sequence shown in SEQ ID NO: 10 and which has glycosylation activity on a flavonoid compound; or (k) a protein which consists of an amino acid sequence sharing an identity of at least 60% or more with the amino acid sequence shown in SEQ ID NO: 10 and which has glycosylation activity on a flavonoid compound.

Another particularly preferred example is a mature protein of the above novel glycosyltransferase protein or a homolog thereof, which is modified to remove a putative secretion signal sequence region, i.e., a protein comprising (p), (q) or (r) shown below (preferably a protein consisting of (p), (q) or (r) shown below):

(p) a protein which consists of the amino acid sequence shown in SEQ ID NO: 26;

(q) a protein which consists of an amino acid sequence comprising substitution, deletion, insertion and/or addition of one or several amino acids in the amino acid sequence shown in SEQ ID NO: 26 and which has glycosylation activity on a flavonoid compound; or (r) a protein which consists of an amino acid sequence sharing an identity of at least 60% or more with the amino acid sequence shown in SEQ ID NO: 26 and which has glycosylation activity on a flavonoid compound.

SEQ ID NO: 25 shows the nucleotide sequence of cDNA encoding TRa2 as a mature protein, i.e., a nucleotide sequence covering nucleotides 61-1389 of SEQ ID NO: 9. Likewise, SEQ ID NO: 26 shows the amino acid sequence of TRa2 as a mature protein, i.e., an amino acid sequence covering amino acids 21-463 of SEQ ID NO: 10.

In addition, the following protein can be presented as an example of glycosyltransferases available for use in the present invention:

a protein having glycosylation activity on a flavonoid compound, which is encoded by a polynucleotide being derived from the genus *Trichoderma* (preferably *Trichoderma viride, Trichoderma reesei, Trichoderma saturnisporum, Trichoderma ghanense, Trichoderma koningii, Trichoderma hamatum, Trichoderma harzianum* or *Trichoderma polysporum*) and comprising any one of the nucleotide sequences shown in SEQ ID NOs: 11 to 24.

A preferred example of such a protein is a protein having glycosylation activity on a flavonoid compound, which is encoded by a polynucleotide comprising any one of the nucleotide sequences shown in SEQ ID NOs: 11 to 24 and sharing high identity with the nucleotide sequence shown in SEQ ID NO: 6, 9 or 25.

It should be noted that the expression "amino acid sequence comprising substitution, deletion, insertion and/or addition of one or several amino acids as used herein does not provide any limitation on the number of amino acids to be substituted, deleted, inserted and/or added, as long as a protein having such an amino acid sequence has desired functions. The number of such amino acids is around 1 to 9 or around 1 to 4, or alternatively, a larger number of amino acids may be substituted, deleted, inserted and/or added as long as such a mutation provides a functionally similar amino acid. Means for preparing a protein having such an amino acid sequence are well known to those skilled in the art. Search and analysis for identity between nucleotide or amino acid sequences may be accomplished by using any algorithm or program (e.g., BLASTN, BLASTX, BLASTP, ClustalW) well known to those skilled in the art. In the case of using a program, parameters may be set as required by those skilled in the art, or alternatively, default parameters specific for each program may be used. Detailed procedures for such analysis are also well known to those skilled in the art. As used herein to describe a nucleotide sequence, the term "high identity" refers to a sequence identity of at least 60% or more, preferably 70% or more, more preferably 80% or more, even more preferably 90% or more, and most preferably 95% or more. As used herein to describe an amino acid sequence, the term "high identity" refers to a sequence identity of at least 60% or more, preferably 70% or more, more preferably 80% or more, even more preferably 90% or more, and most preferably 95% or more.

In the present invention, glycosyltransferases may be used either alone or in combination.

[Glycosyl Donors]

As used herein, the term "glycosyl donor" is intended to mean a carbohydrate which can serve as a substrate for an enzyme in the method of the present invention and can be hydrolyzed to supply a sugar residue to a flavonoid compound, unless otherwise specified. Glycosyl donors available for use in the present invention are carbohydrates containing a maltotriose residue, including maltotriose, maltotetraose, maltopentaose, maltohexaose, maltoheptaose, dextrin, γ-cyclodextrin and soluble starch. As used herein, the term "dextrin" is intended to mean a hydrolysate of starch, unless otherwise specified, while the term "soluble starch" is intended to mean a hydrolysate of starch, which is soluble in hot water, unless otherwise specified. Hydrolysis may be accomplished by using any means such as an acid, heat or an enzyme. In the present invention, it is possible to use a hydrolysate having an average molecular weight of about 3,500 as an example of dextrin and a hydrolysate having an average molecular weight of about 1,000,000 as an example of soluble starch.

[Glycosides]

Glycosides of flavonoid compounds provided by the present invention have the following formula:

[Formula 1]

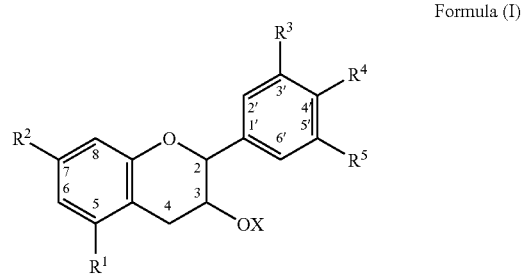

Formula (I)

wherein at least one of $R^1$ to $R^5$ represents a sugar residue, and each of the others represents OH or $OCH_3$, or at least one of $R^1$ to $R^4$ represents a sugar residue and each of the others represents OH or $OCH_3$, and $R^5$ represents H; and X represents H, $CH_3$, a galloyl group or a methylated galloyl group.

This further encompasses glycosides of flavonoid, compounds shown below:

in Formula (I), at least one of $R^1$ to $R^4$ represents an α-linked glucose residue or maltose residue or maltooligosaccharide residue, and each of the others represents OH;

$R^5$ represents OH or H; and

X represents H or a galloyl group.

This further encompasses the glycosides of flavonoid compounds listed below:

5-O-α-D-glucopyranosyl-(+)-catechin;
7-O-α-D-glucopyranosyl-(+)-catechin;
5-O-α-D-glucopyranosyl-(−)-epigallocatechin-3-O-gallate;

7-O-α-D-glucopyranosyl-(−)-epigallocatechin-3-O-gallate;

7-O-(4-O-α-D-glucopyranosyl-α-D-glucopyranosyl)-(−)-epigallocatechin-3-O-gallate;

4'-O-(4-O-α-D-glucopyranosyl-α-D-glucopyranosyl)-(+)-catechin;

4'-O-α-D-glucopyranosyl-(+)-catechin;

3'-O-(4-O-α-D-glucopyranosyl-α-D-glucopyranosyl)-(+)-catechin;

3'-O-α-D-glucopyranosyl-(−)-epigallocatechin-3-O-gallate; and

3'-O-(4-O-α-D-glucopyranosyl-α-D-glucopyranosyl)-(−)-epigallocatechin-3-O-gallate, as well as optical isomers thereof.

Glycosides of flavonoid compounds obtained by the present invention may have increased water solubility when compared to their corresponding flavonoid compounds. For example, 5-O-α-D-glucopyranosyl-(+)-catechin shows at least 40-fold or higher solubility than (+)-catechin, and 5-O-α-D-glucopyranosyl-(−)-epigallocatechin-3-O-gallate is also confirmed to have significantly increased solubility when compared to (−)-epigallocatechin-3-O-gallate (see the Example section). Moreover, glycosylation of flavonoid compounds may also contribute to taste modification of flavonoid compounds. For example, upon glycosylation of a green tea extract rich in (−)-epigallocatechin-3-O-gallate, it has been confirmed that the glycosylated product and individual glycoside components uniformly purified (i.e., 5-O-α-D-glucopyranosyl-(−)-epigallocatechin-3-O-gallate, 7-O-(4-O-α-D-glucopyranosyl-α-D-glucopyranosyl)-(−)-epigallocatechin-3-O-gallate and 7-O-α-D-glucopyranosyl-(−)-epigallocatechin-3-O-gallate) each show a significantly lower level of astringent taste than the unglycosylated product. Likewise, sensorys test made by panelists have also provided the evaluation results indicating reduced bitter and astringent tastes and hence increased drinkability. Furthermore, the studies of the inventors have shown that 4'-O-α-D-glucopyranosyl-(+)-catechin is more stable against heat than catechin. Thus, glycosides of flavonoid compounds obtained by the present invention may have increased heat stability when compared to their corresponding flavonoid compounds.

The present invention therefore provides a method for modifying a flavonoid compound, which comprises the step of treating the flavonoid compound and a glycosyl donor with an enzymatic agent having glycosylation activity and being derived from the genus *Trichoderma* (preferably *Trichoderma viride* or *Trichoderma reesei*). As used herein, the term "modify(ing)" or "modification" is intended to mean at least one of the following: increased water solubility, improved taste and increased stability.

Also in the modification method of the present invention, examples of flavonoid compounds include catechin compounds or methylated derivatives thereof, while examples of glycosyl donors include carbohydrates containing a maltotriose residue (preferably maltotriose, maltotetraose, maltopentaose, maltohexaose, maltoheptaose, dextrin, γ-cyclodextrin or soluble starch). With the aim of increasing the water solubility of flavonoid compounds, enzymatic agents having glycosylation activity and being derived from the genus *Trichoderma* can also be preferred for use, or alternatively, those derived from *Trichoderma viride* and used as cellulase or β-1,3-glucanase may be effective for use. An explanation for each term is as described above.

[Enzymological Properties of the Glycosyltransferase of the Present Invention]

Among glycosyltransferases contained in enzymatic agents available for use in the present invention, particularly preferred is a glycosyltransferase derived from *Trichoderma viride* or *Trichoderma reesei*. This enzyme has the following enzymological features in reaction between flavonoid and glycosyl donor.

Glycosyl Donor Selectivity:

Under the conditions shown in the Example section, this enzyme uses maltotriose, maltotetraose, maltopentaose, maltohexaose, maltoheptaose, soluble starch, dextrin, γ-cyclodextrin or the like as a glycosyl donor, but does not target cellobiose, dextran, maltose monohydrate, carboxymethylcellulose sodium, isomaltooligosaccharide, α-cyclodextrin, β-cyclodextrin or the like as a glycosyl donor. Moreover, this enzyme is a glycosyltransferase capable of producing not only sugars composed of one or two glucose molecules, but also glycosides whose sugar chain length is three (G3) or more glucose molecules.

Substrate Specificity:

This enzyme can act on and glycosylate a wide range of polyphenols including major flavonoid members such as catechin, epigallocatechin gallate, naringenin, quercetin, daidzein, genistein and kaempferol, as well as esculetin.

Reaction Optimum pH and Temperature:

This enzyme allows a satisfactory reaction at a pH of about 4.5 to about 7.0, particularly about 5.0 to about 6.5, or at a temperature of about 30° C. to about 55° C., particularly about 45° C. to about 55° C., under the conditions shown in the Example section.

[Uses of Glycosides]

Glycosides obtained by the present invention can be used as food compositions, pharmaceutical compositions or cosmetic compositions. More specifically, for example, such a composition incorporating a glycoside of a catechin compound can be used as an agent for the following purposes, as in the case of catechin: anti-allergy, anti-oxidation, anti-cancer, anti-inflammation, anti-bacteria/anti-caries, anti-virus, detoxication, intestinal flora improvement, odor elimination, anti-hypercholesterolemia, anti-hypertension, anti-hyperglycemia, anti-thrombosis, dementia prevention, body fat burning, inhibition of body fat accumulation, endurance improvement, anti-fatigue or renal function improvement, or alternatively, can also be used as a food composition, a pharmaceutical composition or a cosmetic composition.

Food compositions include nutritional supplementary foods, health foods, therapeutic dietary foods, general health foods, supplements and beverages. Beverages include tea beverages, juices, soft drinks, and drinkable preparations. Pharmaceutical compositions may be prepared as drugs or quasi drugs, preferably oral formulations or dermatologic external preparations, and may be provided in the form of solutions, tablets, granules, pills, syrups, lotions, sprays, plasters or ointments. Cosmetic compositions may be provided in the form of creams, liquid lotions, emulsion lotions or sprays.

The amount of glycoside(s) incorporated into the food, pharmaceutical or cosmetic composition of the present invention is not limited in any way and may be designed as required by those skilled in the art in consideration of, e.g., solubility and taste by referring to preferred daily intakes of the corresponding flavonoid compound(s). For example, the amount of the glycoside(s) of the present invention incorporated into a composition may be set to 0.01% to 99.9% by weight or may be determined such that the glycoside(s) of the present invention can be given 100 mg to 20 g per day as a single dose or in divided doses (e.g., three doses).

The food, pharmaceutical or cosmetic composition of the present invention may further comprise various ingredients acceptable for food, pharmaceutical or cosmetic purposes. Examples of these additives and/or ingredients include vitamins, saccharides, excipients, disintegrating agents, binders, lubricants, emulsifiers, isotonizing agents, buffers, solubilizers, antiseptics, stabilizers, antioxidants, coloring agents, correctives, flavorings, coagulating agents, pH adjustors, thickeners, tea extracts, herbal extracts, and minerals.

[Other Embodiments]

In the present invention, an enzyme protein contained in an enzymatic agent can be immobilized on an appropriate carrier for use as an immobilized enzyme. As a carrier, any conventional resin used for the same purpose may be used, including basic resins (e.g., MARATHON WBA (Dow Chemical), SA series, WA series or FP series (Mitsubishi Chemical Corporation, Japan), and Amberlite IRA904 (Organo)), as well as hydrophobic resins (e.g., Diaion FPHA13 (Mitsubishi Chemical Corporation, Japan), HP series (Mitsubishi Chemical Corporation, Japan), and Amberlite XAD7 (Organo)). In addition, other resins such as Express-Ion D (Whatman), DEAE-Toyopearl 650M (Tosoh Corporation, Japan) and DEAE-sepharose CL4B (Amersham Biosciences) may be preferred for use. Any conventional technique can be used for enzyme immobilization, as exemplified by physical adsorption, the binding method which uses ionic or covalent binding for immobilization, the crosslinking method which uses a reagent having a divalent functional group for immobilization through crosslinking, and the entrapping method which embeds an enzyme within a gel or semipermeable membrane of network structure. For example, immobilization may be accomplished by allowing an enzyme (20 to 2,000 mg, e.g., 50 to 400 mg) in distilled water to be adsorbed to 5 ml of each resin, followed by removal of the supernatant and drying.

The present invention also provides an enzymatic agent for glycosylating a flavonoid compound, which comprises an enzyme having glycosylation activity and being derived from the genus *Trichoderma* (e.g., *Trichoderma viride, Trichoderma reesei, Trichoderma saturnisporum, Trichoderma ghanense, Trichoderma koningii, Trichoderma hamatum, Trichoderma harzianum* or *Trichoderma polysporum*, preferably *Trichoderma viride*). Such an enzymatic agent comprises one or more glycosidases derived from ascomycetous filamentous fungi, and may further comprise other additives (e.g., enzyme-stabilizing components, glycosyl donor components, other enzymes).

ADVANTAGES OF THE INVENTION

The present invention allows efficient glycosylation of flavonoid compounds. In particular, the present invention allows efficient glycosylation at the 5-, 7-, 3'- and/or 4'-positions of catechin compounds.

The present invention allows glycosylation of flavonoid compounds to thereby improve their water solubility. This suggests that the present invention can enhance the oral absorption of flavonoid compounds. Moreover, improved water solubility will contribute to not only improvement of dissolution rate in water, but also improvement of absorption rate in the body. Thus, the present invention allows flavonoid compounds to exert their useful activity (e.g., antioxidative activity) in vivo with high efficiency.

The present invention can also modify the taste of flavonoid compounds through glycosylation. Particularly when a flavonoid compound having bitter and astringent tastes like a catechin compound is glycosylated in accordance with the present invention, such tastes can be reduced.

The present invention can also improve the heat stability of flavonoid through glycosylation.

BRIEF DESCRIPTION OF THE DRAWINGS

FIG. 3 shows an alignment of 4 amino acid sequences in Group 1 of FIG. 2, along with their highly conserved regions (underlined). FIG. 3 discloses SEQ ID NOS: 28-31, respectively, in order of appearance.

FIG. 4 shows a comparison between genomic DNA sequence (SEQ ID NO: 6) and cDNA sequence (SEQ ID NO: 9) of TRa2.

FIG. 5 shows the cDNA nucleotide sequence (SEQ ID NO: 9) of TRa2 and its corresponding deduced amino acid sequence (SEQ ID NO: 10). The double-underlined part represents a putative secretion signal sequence.

FIG. 6 shows a comparison of the primary structure between the deduced amino acid sequence of TRa2 (SEQ ID NO: 32)and the Taka-amylase precursor amino acid sequence (GB No. BAA00336) (SEQ ID NO: 33). Underlined: putative secretion signal of TRa2; broken-underlined: secretion signal of Taka-amylase; double-underlined: 4 regions highly conserved among α-amylase family enzymes; and amino acid residues indicated with *: amino acid residues located at catalytic sites.

EXAMPLES

Example 1

Catechin Glycosylation Activity in *Trichoderma* Culture

Figure 1:
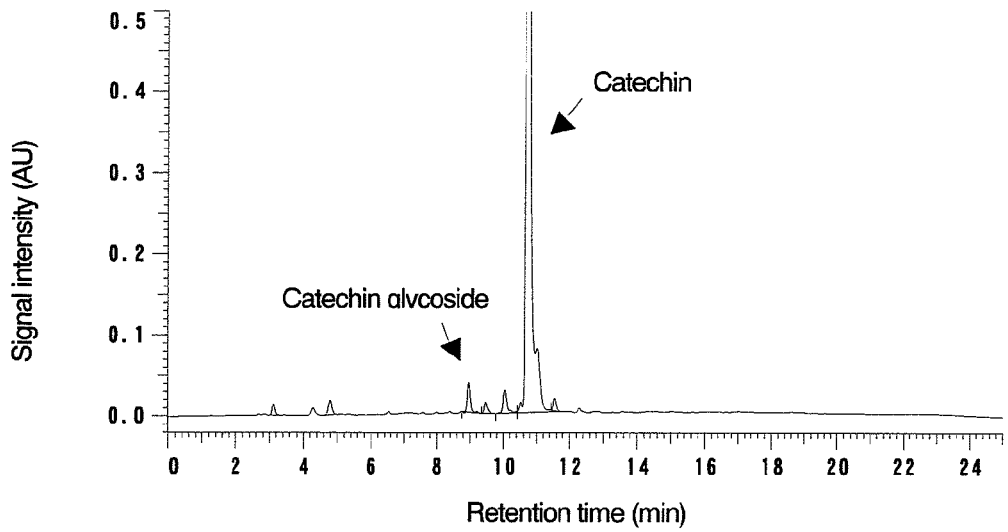
FIG. 1 shows an HPLC analysis chart of catechin when treated with a crude enzyme solution of *Trichoderma viride* IAM5141.

*Trichoderma viride* strain IAM5141 was inoculated from a slant into a liquid medium (10 ml) containing 1% yeast extract (Difco), 1% polypeptone (Nihon Pharmaceutical Co., Ltd., Japan) and 2% dextrin (Nacalai Tesque, Inc., Japan), followed by shaking culture at 30° C. for 1 day to give a pre-cultured solution. Further, the entire volume of the pre-cultured solution was inoculated into 900 ml of the same liquid medium and cultured at 30° C. for 3 days, followed by filter filtration to prepare a culture supernatant solution. After addition of ammonium sulfate (387 g, 80% saturation) to the culture supernatant (690 ml), the mixture was stirred and centrifuged to collect a precipitate. The resulting precipitate was diluted with 10 ml of 0.1 M acetate buffer (pH 5.0) for use as a crude enzyme solution.

To the crude enzyme solution (100 μl), catechin (3 mg) and dextrin (10 mg) were added and stirred at 50° C. for 24 hours to cause an enzyme reaction. The reaction solution was diluted 10-fold with 0.1% trifluoroacetic acid (TFA), 10 μl of which was then analyzed by high performance liquid chromatography (HPLC).

Analysis Conditions
Column: Develosil C30-UG-5 (4.6×150 mm)
Gradient conditions: 5% Eluent B→50% Eluent B/20 min
Eluent A: 0.1% TFA/distilled water
Eluent B: 90% acetonitrile/0.08% TFA
Flow rate: 1 ml/min
Detection wavelength: 280 nm As shown in FIG. 1, the results confirmed the generation of a catechin glycoside through the above reaction. Moreover, it was also confirmed that a similar glycoside was generated in the case of using γ-cyclodextrin as a glycosyl donor. These results suggest that *T. viride* strain IAM5141 produces and secretes an enzyme which glycosylates catechin using dextrin or γ-cyclodextrin as a glycosyl donor.

Example 2

Properties of Various Enzymatic Agents Derived from the Genus *Trichoderma*

(+)-Catechin (3 mg) was dissolved in 100 μl of 0.1 M acetate buffer (pH 5) and mixed with each enzymatic agent (10 mg or 10 μl) and soluble starch (10 mg, Nacalai Tesque, Inc., Japan) or dextrin (10 mg), followed by stirring at 50° C. for 1 day. After the reaction, the centrifuged supernatant was diluted 10-fold and analyzed by HPLC. Analysis conditions were set as shown in Example 1.

The enzymatic agents used are shown in the table below, along with their experimental results.

TABLE 1

| Supplier | Enzymatic agent | Glycosyl donor | Product (% area) 7-Glc | Product (% area) 5-Glc |
|---|---|---|---|---|
| Yakult Pharmaceutical Industry | Cellulase "Onozuka" derived from *Trichoderma viride* | none SS Dex | — 2.86 2.93 | — 8.79 8.97 |
| Yakult | Cellulase "Onozuka" RS | none | — | — |
| Pharmaceutical Industry | derived from *Trichoderma viride* | SS Dex | 2.21 1.70 | 9.21 7.95 |
| Yakult | Cellulase "Onozuka" R-10 | none | — | — |
| Pharmaceutical Industry | derived from *Trichoderma viride* | SS Dex | — — | 7.68 5.98 |
| Yakult | Cellulase "Onozuka" FA | none | — | — |
| Pharmaceutical Industry | derived from *Trichoderma viride* | SS Dex | 2.92 2.82 | 8.78 9.14 |
| Yakult | Fancellase | none | — | — |
| Pharmaceutical Industry | β-1,3-glucanase | SS Dex | — — | 2.51 1.70 |
| Yakult | Pancellase SS | none | — | — |
| Pharmaceutical Industry | derived from *Trichoderma viride* cellulase | SS Dex | 2.18 1.94 | 8.17 7.05 |
| Yakult | Pancellase BR | none | — | — |
| Pharmaceutical Industry | derived from *Trichoderma viride* 5% cellulase + 95% lactose | SS Dex | 2.86 3.19 | 8.30 9.94 |
| Yakult | Cellulase "Onozuka" 3S | none | — | — |
| Pharmaceutical Industry | derived from *Trichoderma viride* | SS Dex | 3.04 2.51 | 9.85 9.28 |
| Amano Enzyme | Cellulase T "Amano" 4 derived from *Trichoderma viride* 16% cellulase + dextrin | none SS Dex | 0.94 1.98 1.41 | 2.86 6.00 4.19 |
| Amano Enzyme | Cellulase XP-425 | none SS Dex | 1.71 3.27 3.09 | 5.82 9.54 8.47 |
| SIGMA | Cellulase derived from *Trichoderma viride* | none SS Dex | — 2.57 1.36 | 2.07 10.99 6.17 |

None: absence,
SS: soluble starch,
Dex: dextrin
7-Glc: 7-O-α-D-glucopyranosyl-(+)-catechin
5-Glc: 5-O-α-D-glucopyranosyl-(+)-catechin It was found that glycosylation activity on catechin compounds was observed for a wide range of enzymatic agents derived from the genus *Trichoderma*, which are commercially available as cellulase from different suppliers.

Example 3

Preparation of Flavonoid Glycosides (1)

a. Preparation of 5-O-α-D-glucopyranosyl-(+)-catechin and 7-O-α-D-glucopyranosyl-(+)-catechin (+)-Catechin (60 mg) was mixed with soluble starch (200 mg, Nacalai Tesque, Inc., Japan), Cellulase T "Amano" 4 (200 mg, Amano Enzyme Inc., Japan) and 0.1 M acetate buffer (2 ml, pH 5), followed by stirring at 50° C. for 3 days. After the reaction, the centrifuged supernatant was fractionated and purified under the following conditions: column: Develosil C30-UG-5 (20×250 mm, Nomura Chemical Co., Ltd., Japan), Eluent A: 0.1% TFA/distilled water, Eluent B: 90% acetonitrile/0.08% TFA, elution conditions: 20% Eluent B, flow rate: 4 ml/min, detection wavelength: 280 nm. The generated main peak fraction was collected and lyophilized to prepare a standard.

7-O-α-D-glucopyranosyl-(+)-catechin: m/z 450.9, NMR: δ ppm (D$_2$O); 2.48 (1H, dd), 2.80 (1H, dd), 3.42 (1H, t), 3.4-3.7 (4H, m), 3.80 (1H, t), 4.14 (1H, q), 4.69 (1H, d), 5.47 (1H, d), 6.23 (1H, d), 6.27 (1H, d), 6.78 (1H, dd), 6.84 (1H, d), 6.86 (1H, d).

5-O-α-D-glucopyranosyl-(+)-catechin: m/z 450.8, NMR δ ppm (D$_2$O); 2.62 (1H, dd), 2.81 (1H, dd), 3.43 (1H, t), 3.45-

3.55 (1H, m), 3.6-3.7 (3H, m), 3.83 (1H, t), 4.18 (1H, dd), 4.76 (1H, d), 5.61 (1H, d), 6.09 (1H, d), 6.31 (1H, d), 6.77 (1H, d), 6.8-6.9 (2H, m).

b. Preparation of 5-O-α-D-glucopyranosyl-(−)-epigallocatechin-3-O-gallate (−)-Epigallocatechin-3-O-gallate (120 mg) was mixed with dextrin (400 mg, Nacalai Tesque, Inc., Japan), Cellulase "Onozuka" RS (400 mg, Yakult Pharmaceutical Industry Co., Ltd., Japan) and 0.1 M acetate buffer (3 ml, pH 5), followed by stirring at 50° C. for 3 days. After the reaction, the centrifuged supernatant was fractionated and purified under the following conditions: column: Develosil C30-UG-5 (20×250 mm), elution conditions: 40% methanol, flow rate: 3 ml/min, detection wavelength: 280 nm. The main peak fraction was 5-O-α-D-glucopyranosyl-(−)-epigallocatechin-3-O-gallate.

5-O-α-D-glucopyranosyl-(−)-epigallocatechin-3-O-gallate: m/z 621.0, NMR δ ppm ($D_2O$); 2.8-3.1 (2H, m), 3.52 (1H, t), 3.7-3.8 (4H, m), 3.91 (1H, t), 5.01 (1H, s), 5.54 (1H, s), 5.6 (1H, broad s), 6.35 (1H, s), 6.43 (1H, s), 6.57 (2H, s), 6.95 (2H, s).

c. Preparation of 7-O-α-D-glucopyranosyl-(−)-epigallocatechin-3-O-gallate and 7-O-(4-O-α-D-glucopyranosyl-α-D-glucopyranosyl)-(−)-epigallocatechin-3-O-gallate Epigallocatechin gallate (3 g) was mixed with Pancellase BR (5 g, Yakult Pharmaceutical Industry Co., Ltd., Japan), dextrin (10 g) and 0.1 M acetate buffer (100 ml, pH 5), followed by stirring at 50° C. for 4 hours. After the reaction, the centrifuged supernatant was adsorbed onto a Sepharose LH20 (100 ml, Amersham Biosciences) column. After stepwise elution with distilled water (200 ml), 30% ethanol (200 ml) and 40% ethanol (200 ml), glycoside fractions were collected to prepare a lyophilized product, 50 mg of which was further dissolved in distilled water (5 ml) and then fractionated and purified under the following conditions: column: Develosil C30-UG-5 (20×250 mm), Eluent A:0.1% TFA/distilled water, Eluent B:90% methanol/0.1% TFA, elution conditions: 30% B, flow rate: 3 ml/min, detection wavelength: 280 nm. As major components, 7-O-α-D-glucopyranosyl-(−)-epigallocatechin-3-O-gallate and 7-O-(4-O-α-D-glucopyranosyl-α-D-glucopyranosyl)-(−)-epigallocatechin-3-O-gallate were obtained.

7-O-α-D-glucopyranosyl-(−)-epigallocatechin-3-O-gallate: m/z 621.1, NMR δ ppm ($D_2O$); 2.98 (1H, d), 3.08 (1H, d), 3.53 (1H, t), 3.68 (1H, s), 3.7-3.9 (3H, m), 3.92 (1H, t), 5.14 (1H, s), 5.62 (2H, broad s), 6.40 (1H, s), 6.48 (1H, s), 6.61 (2H, s), 6.99 (2H, s).

7-O-(4-O-α-D-glucopyranosyl-α-D-glucopyranosyl)-(−)-epigallocatechin-3-O-gallate: m/z 783.1, NMR δ ppm (D2O); 2.93 (1H, dd), 3.00 (1H, dd), 3.43 (1H, t), 3.60 (1H, dd), 3.7-3.9 (9H, m), 4.18 (1H, t), 4.96 (1H, s), 5.21 (1H, d), 5.51 (1H, bs), 5.59 (1H, d), 6.35 (1H, d), 6.43 (1H, d), 6.57 (2H, s), 6.96 (2H, s).

Example 4

Preparation of Flavonoid Glycosides (2)

1. PCR Cloning of Partial α-amylase Homolog Sequences

In view of the facts that dextrin and γ-cyclodextrin are polymers in which glucose residues are linked through α-1,4 linkages and that the intended enzyme has the ability to degrade these polymers, it is suggested that the enzyme may be an α-amylase family-like enzyme.

Figure 2:
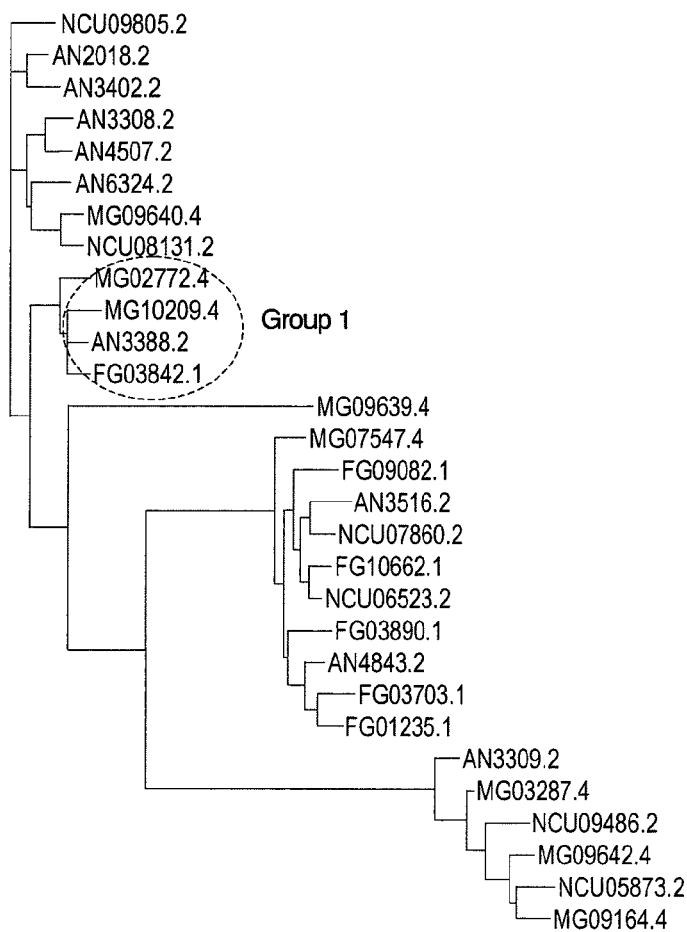
FIG. 2 shows a dendrogram prepared by a dendrogram preparation program, Tree view, with respect to the amino acid sequences of putative ORFs having the alpha-amylase catalytic domain (accession No. PF00128) motif extracted from the genomic information databases of *Aspergillus nidulans, Neurospora crassa, Magnaporthe grisea* and *Fusarium graminearum*.

For further study, with respect to a putative ORF having the alpha-amylase catalytic domain (accession No. PF00128) motif in the protein family database (PFAM), 9, 6, 8 and 6 amino acid sequences were extracted from the genomic information databases of *Aspergillus nidulans, Neurospora crassa, Magnaporthe grisea* and *Fusarium graminearum*, respectively, among microorganisms belonging to the same ascomycetous filamentous fungi as *Trichoderma* and already identified for their genome sequences. For these sequences, an alignment was prepared by the homology search program ClustalW and a dendrogram was prepared by the dendrogram preparation program Tree view, whereby the sequences were grouped on the basis of their homology. Four amino acid sequences in Group 1 of FIG. 2, i.e., MG02772.4 (EAA47529), MG10209.4 (EAA48146), AN3388.2 (EAA63356) and FG03842.1 (EAA71544) (numbers in parentheses are Genebank Accession Nos.) were aligned to synthesize oligo DNAs corresponding to the amino acid sequences of their highly conserved regions (FIG. 3, underlined).

```
AMY-12f:
5'-TAYTGYGGNGGNACNTTYAARGGNYT-3'    (SEQ ID NO: 1)

AMY-15r:
5'-TTYTCNACRTGYTTNACNGTRTCDAT-3'   (SEQ ID NO: 2)

AMY-17r:
5'-GGTNAYRTCYTCNCKRTTNGCNGGRTC-3'  (SEQ ID NO: 3)
```

From wet cells (about 1 g) of *T. viride* IAM5141 cultured as described above, genomic DNA was extracted with a DNeasy plant Maxi Kit (QIAGEN). This genomic DNA (50 ng) was used as a template to perform PCR reaction with primers AMY-12f and AMY-15r or primers AMY-12f and AMY-17r. Namely, PCR was accomplished by using ExTaq (Takara Bio Inc., Japan) under the following conditions: 94° C. for 2 minutes, (94° C. for 1 minute, 50° C. for 1 minute, 72° C. for 1 minute)×30 cycles, and 72° C. for 10 minutes. The PCR products were analyzed by agarose gel electrophoresis, confirming a fragment of approximately 0.6 kbp for the primer combination of AMY-12f and AMY-15r and a fragment of approximately 1.0 kbp for the primer combination of AMY-12f and AMY-17r. Then, these DNA fragments were excised from the agarose gel and purified with a GFX PCR DNA and Gel Band Purification Kit (Amersham Biosciences). Each DNA was cloned with a TOPO-TA cloning kit (Invitrogen) and analyzed for its nucleotide sequence using an ABI 3100 Avant (Applied Biosystems). The nucleotide sequence obtained for the former fragment was included within the nucleotide sequence obtained for the latter fragment. A homology search with Blastx was made for this nucleotide sequence against amino acid sequences registered in GenBank, indicating that the highest homology was observed with MG10209.4 (EAA48146).

2. Genome Sequence Determination of Amylase Homolog

On the basis of the resulting nucleotide sequence of approximately 1.0 kbp, the following primers were designed and used to perform Inverse PCR.

```
TRa2-2:
5'-CCAACCTGGTATCTACATAC-3'    (SEQ ID NO: 4)

TRa2-3:
5'-AGATGGCATCAAATCCCAT-3'     (SEQ ID NO: 5)
```

Figure 4:
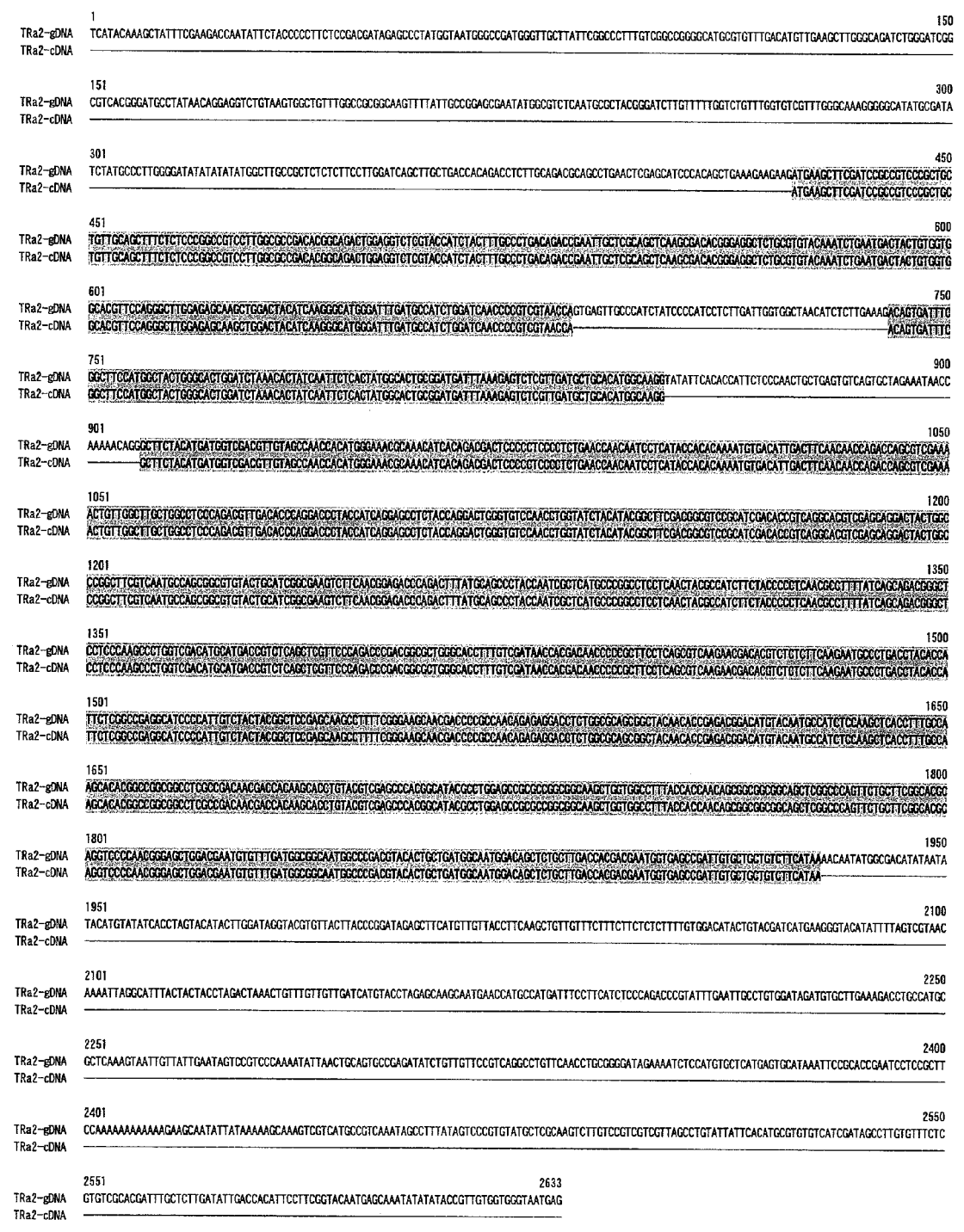

First, the genomic DNA prepared from *T. viride* IAM5141 was completely digested with HindIII or PstI, and then closed by self-ligation through overnight incubation at 16° C. with ligation high (Toyobo Co., Ltd., Japan). These DNAs (0.1 μg each) were each used as a template to perform PCR reaction with the above primers TRa2-2 and TRa2-3. PCR was accomplished by using LA Taq (Takara Bio Inc., Japan) under the following conditions: 94° C. for 2 minutes, (95° C. for 30 seconds, 66° C. for 15 minutes)×30 cycles, and 72° C. for 10 minutes. The resulting PCR products were analyzed by agarose gel electrophoresis, confirming a DNA fragment of approximately 2 kb for the case of using the HindIII-digested genomic DNA as a template, and a DNA fragment of approximately 4.5 kb for the case of using the PstI-digested genome as a template. These DNA fragments were each excised from the agarose gel and cloned in the same manner as described above. Nucleotide sequences were determined from both ends of the inserted fragments. The nucleotide sequences from the HindIII-digested genome and the PstI-digested genome were found to overlap with each other until reaching the restriction enzyme sites. The nucleotide sequences thus obtained were ligated to the partial sequence previously obtained. This nucleotide sequence is shown in FIG. 4 (TRa2-gDNA) and SEQ ID NO: 6. The coding region of the α-amylase homolog was deduced by comparison with the 4 sequences in Group 1 of FIG. 2, appearance of an initiation codon and a termination codon, etc. The initiation codon was considered to be ATG at nucleotides 423-425, while the termination codon was considered to be TAA at nucleotides 1926-1928.

3. cDNA Cloning of α-amylase Homolog

From the *T. viride* strain IAM5141 cells (about 0.1 g) cultured as described above, total RNA was extracted with an RNeasy plant mini kit. The total RNA (1 μg) was used for cDNA synthesis in a SuperScript First-Strand system for RT-PCR(Invitrogen) using random hexamers.

On the basis of the genome sequence previously obtained, the following primers were designed.

```
TRa2EcoRI-f2:
5'-GGAATTCATGAAGCTTCGATCCGCCGTCCC-3' (SEQ ID NO: 7)

TRa2XhoI-r2:
5'-CCGCTCGAGTTATGAAGACAGCAGCACAAT-3' (SEQ ID NO: 8)
```

The synthesized cDNA was used as a template to perform PCR reaction with the above primers TRa2EcoRI-f2 and TRa2XhoI-r2. PCR was accomplished by using Ex Taq (Takara Bio Inc., Japan) under the following conditions: 94° C. for 2 minutes, (94° C. for 1 minute, 55° C. for 1 minute, 72° C. for 2 minutes)×30 cycles, and 72° C. for 10 minutes. The resulting PCR products were analyzed by agarose gel electrophoresis, confirming a DNA fragment of approximately 1.5 kb. This DNA fragment was excised from the agarose gel and purified by GFX. The resulting DNA fragment was cloned with a TOPO-TA cloning kit (Invitrogen) to construct plasmid pCRTRa2-cDNA, and the nucleotide sequence of the cDNA was determined (FIG. 4, FIG. 5 and SEQ ID NO: 9). The genomic DNA sequence previously obtained was compared with the cDNA sequence thus obtained, indicating that the genome sequence contained two introns (FIG. 4). The cDNA sequence was found to contain 1392 by ORF encoding a protein composed of 463 amino acid residues (FIG. 5 and SEQ ID NO: 10). This gene was designated as TRa2. When the deduced amino acid sequence encoded by this gene was analyzed by Signal P (Nielsen H. et. al., Protein Eng., 10, 1-6, 1997), the N-terminal 20 amino acid residues appeared to constitute a secretion signal sequence. Further, a homology search was made for the deduced amino acid sequence encoded by TRa2 in the same manner as described above, indicating that the highest homology was observed with AN3388.2 (EAA63356). The deduced amino acid sequence of TRa2 protein was compared with the amino acid sequence of Taka-amylase, which is a known α-amylase. The result indicated that 4 conserved regions among α-amylase family enzymes were also conserved in this enzyme (FIG. 6, double-underlined), and that the aspartic acid residue, the glutamic acid residue and the aspartic acid residue, each serving as an active center, were all conserved (FIG. 6, amino acid residues indicated with *).

4. Construction of Secretory Expression System for TRa2 Protein in Yeast

The plasmid pCRTRa2-cDNA was digested with restriction enzymes EcoRI and XhoI to give a fragment of approximately 1.5 kb, which was then ligated to an EcoRI- and SalI-digested fragment of plasmid pYE22m (Biosci. Biotech. Biochem., 59(7), 1221-1228, 1995) using ligation high (Toyobo Co., Ltd., Japan) to thereby obtain plasmid pYETRa2.

The plasmid pYETRa2 was used to transform yeast *S. cerevisiae* strain EH1315 by the lithium acetate method. The resulting transformed strain was designated as strain TRa2-1. A loopful of the strain TRa2-1 was inoculated into 10 ml YPD (Difco) liquid medium and cultured with shaking at 30° C. for 2 days. Since the TRa2 protein has a secretion signal sequence composed of 20 amino acid residues at its N-terminal end, the protein was considered to be secreted into a culture solution. Then, the yeast cells were precipitated by centrifugation to collect the culture supernatant.

5. Measurement of Glycosidase Activity of TRa2

The culture supernatant (500 μl) was concentrated about 5-fold using Microcon YM-30 (Amicon). The above concentrate (10 μl) was added to 100 μl of 20 mM acetate buffer (pH 5.0) containing 0.5% maltose, maltotriose, maltotetraose, dextrin, α-cyclodextrin, β-cyclodextrin or γ-cyclodextrin, and reacted at 50° C. for 1 hour.

After completion of the reaction, each sample was analyzed by TLC as follows. The plate used was a silica gel G-60 plate (Merck & Co., Inc.), and the developing solution used was 2-propanol:acetone:0.5 M lactic acid=2:2:1. For detection, the plate was sprayed with sulfuric acid:ethanol=1:9, air-dried and then heated on a hot plate. As a result, none of the sugars was degraded in a culture solution of the control strain (strain C-1) transformed with vector pYE22m. In contrast, in a culture solution of the strain TRa2-1, maltotriose, maltotetraose, dextrin and γ-cyclodextrin were degraded to mainly generate maltose and glucose, but there was no degradation of maltose, α-cyclodextrin and β-cyclodextrin.

6. Measurement of Glycosylation Activity of TRa2

Figure 7:
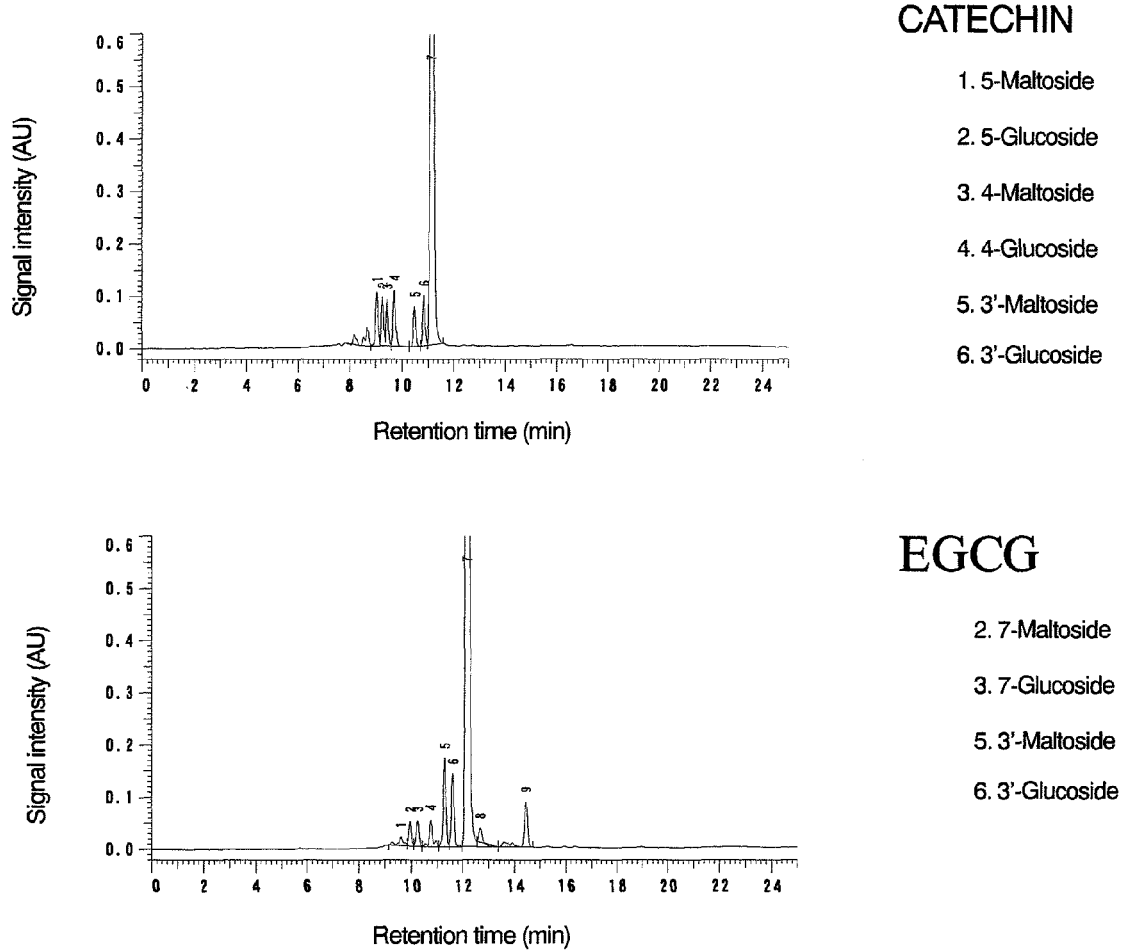
FIG. 7 shows HPLC analysis charts of the reaction solution when (+)-catechin or (−)-epigallocatechin-3-O-gallate and dextrin were added to and reacted in a culture supernatant stock of a transformant (strain TRa2-1) or a concentrate thereof.

To 100 μl of a culture supernatant stock or a concentrate thereof concentrated about 5-fold with a VIVASPIN 10,000 MWCO/PES (VIVASCIENCE), (+)-catechin or (−)-epigallocatechin-3-O-gallate (3 mg) and dextrin (10 mg) were added and reacted with stirring at 50° C. for 1 day. After completion of the reaction, the reaction solution was diluted 10-fold with a 0.1% trifluoroacetic acid solution and analyzed by high performance liquid chromatography (HPLC) under the same conditions as used in Example 1. As a result, no reaction product was observed in the reaction solution reacted with the culture supernatant from the control strain (strain C-1) transformed with vector pYE22m, whereas the generation of catechin glycosides and epigallocatechin-3-O-gallate glycosides was confirmed in the case of the strain TRa2-1 (FIG. 7).

7. TRa2-catalyzed Preparation of Catechin Glycosides

The strain TRa2-1 was inoculated into 200 ml YPD liquid medium and cultured with shaking at 30° C. for 3 days. The cells were collected by centrifugation to obtain the culture supernatant. This culture supernatant (100 ml) was concentrated to 50 ml using a ultrafiltration disk NMWL 30000/regenerated cellulose while adding 100 ml of 0.1 M acetate buffer (pH 5), and used as a TRa2 enzyme solution. The above TRa2 enzyme solution (50 ml) was mixed with (+)-catechin (1.5 g) and dextrin (5 g), followed by stirring at 45° C. for 18 hr. The reaction solution was centrifuged, and the supernatant was adsorbed onto a LH20 (Amersham Biosciences) resin 60 ml/φ2.5×20 cm column. After elution with distilled water (120 ml) and 10% ethanol (240 ml), glycoside fractions were collected and lyophilized to give 530 mg lyophilized powder, 50 mg of which was then dissolved in 5 ml distilled water and separated on a Develosil C30-UG-5 column 20×250 mm, A: 0.1% TFA/distilled water, B: 90% methanol/0.1% TFA, 30% B, 3 ml/min, 280 nm. Peaks 1 to 6 were collected and lyophilized in the order in which they were eluted from the HPLC column. MS and NMR analyses suggested that Peak 1 was 5-O-(4-O-α-D-glucopyranosyl-α-D-glucopyranosyl)-(+)-catechin, Peak 2 was 5-O-α-D-glucopyranosyl-(+)-catechin, Peak 3 was 4'-O-(4-O-α-D-glucopyranosyl-α-D-glucopyranosyl)-(+)-catechin, Peak 4 was 4'-O-α-D-glucopyranosyl-(+)-catechin, Peak 5 was 3'-O-(4-O-α-D-glucopyranosyl-α-D-glucopyranosyl)-(+)-catechin, and Peak 6 was 3'-O-α-D-glucopyranosyl-(+)-catechin.

5-O-(4-O-α-D-glucopyranosyl-α-D-glucopyranosyl)-(+)-catechin: m/z 615.2, NMR δ ppm (D$_2$O); 2.71 (1H, dd), 2.85 (1H, dd), 3.42 (1H, t), 3.56-3.85 (9H, m), 4.19 (1H, t), 4.26 (1H, dd), 4.87 (1H, d), 5.70 (1H, d), 6.19 (1H, d), 6.39 (1H, d), 6.83 (1H, dd), 6.90-6.93 (2H, m).

5-O-α-D-glucopyranosyl-(+)-catechin: m/z 453.2, NMR δ ppm (D$_2$O); 2.62 (1H, dd), 2.81 (1H, dd), 3.43 (1H, t), 3.45-3.55 (1H, m), 3.6-3.7 (3H, m), 3.83 (1H, t), 4.18 (1H, dd), 4.76 (1H, d), 5.61 (1H, d), 6.09 (1H, d), 6.31 (1H, d), 6.77 (1H, d), 6.8-6.9 (2H, m).

4'-O-(4-O-α-D-glucopyranosyl-α-D-glucopyranosyl)-(+)-catechin: m/z 615.2, NMR δ ppm (D$_2$O); 2.54 (1H, dd), 2.81 (1H, dd), 3.43 (1H, t), 3.60 (1H, dd), 3.68-3.94 (9H, m), 4.19-4.28 (2H, m), 4.82 (1H, d), 5.44 (1H, d), 5.62 (1H, d), 6.04 (1H, d), 6.11 (1H, d), 6.91 (1H, dd), 7.00 (1H, d), 7.22 (1H, d).

4'-O-α-D-glucopyranosyl-(+)-catechin: m/z 453.2, NMR δ ppm (D$_2$O); 2.45 (1H, dd), 2.73 (1H, dd), 3.45 (1H, t), 3.65-3.75 (4H, m), 4.11 (1H, dd), 4.7-4.75 (2H, m), 5.53 (1H, d), 5.95 (1H, d), 6.02 (1H, d), 6.83 (1H, d), 6.91 (1H, d), 7.15 (1H, d).

3'-O-(4-O-α-D-glucopyranosyl-α-D-glucopyranosyl)-(+)-catechin: m/z 615.2, NMR δ ppm (D$_2$O); 2.54 (1H, dd), 2.80 (1H, dd), 3.44 (1H, t), 3.59 (1H, dd), 3.67-3.90 (9H, m), 4.17-4.24 (2H, m), 4.83 (1H, d), 5.41 (1H, d), 5.55 (1H, d), 6.03 (1H, d), 6.10 (1H, d), 7.10 (1H, d), 7.06 (1H, d), 7.26 (1H, d).

3'-O-α-D-glucopyranosyl-(+)-catechin: m/z 453.2, NMR δ ppm (D$_2$O); 2.43 (1H, dd), 2.73 (1H, dd), 3.27 (1H, s), 3.44 (1H, t), 3.6-3.7 (4H, m), 3.88 (1H, t), 4.10 (1H, dd), 4.69 (1H, d), 5.46 (1H, d), 5.93 (1H, s), 6.01 (1H, s), 6.89 (1H, d), 6.94 (1H, dd), 7.18 (1H, d).

8. TRa2-catalyzed Preparation of Epigallocatechin-3-O-gallate Glycosides

The strain TRa2-1 was inoculated into 100 ml YPD liquid medium and cultured with shaking at 30° C. for 3 days. The cells were collected by centrifugation to obtain the culture supernatant. This culture supernatant (45 ml) was concentrated to 20 ml using a ultrafiltration disk NMWL 30000/regenerated cellulose while adding 50 ml of 0.1 M acetate buffer (pH 5), and used as a TRa2 enzyme solution. This TRa2 enzyme solution (20 ml) was mixed with (−)-epigallocatechin-3-O-gallate (600 mg) and dextrin (2 g), followed by stirring at 50° C. for 1 day. The reaction solution was centrifuged, and the supernatant was adsorbed onto a LH20 resin 25 ml/φ1.5×30 cm column. After elution with distilled water (100 ml), 10% ethanol (100 ml), 20% ethanol (100 ml) and 30% ethanol (200 ml), the 30% ethanol fraction was collected and lyophilized. The lyophilized powder (120 mg) was dissolved in 12 ml distilled water and separated on a Develosil C30-UG-5 column 20×250 mm, A: 0.1% TFA/distilled water, B: 90% methanol/0.1% TFA, 40% B, 3 ml/min, 280 nm. MS and NMR analyses suggested that Peak 2 was 7-O-(4-O-α-D-glucopyranosyl-α-D-glucopyranosyl)-(−)-epigallocatechin-3-O-gallate, Peak 5 was 3'-O-(4-O-α-D-glucopyranosyl-α-D-glucopyranosyl)-(−)-epigallocatechin-3-O-gallate, and Peak 6 was 3'-O-α-D-glucopyranosyl-(−)-epigallocatechin-3-O-gallate. In contrast, Peak 3 was suggested to be a mixture of glucoside and maltotetraoside, as judged by its MS data (m/z 621.2, 1107.3), and the glucoside was considered to be 7-O-α-D-glucopyranosyl-(−)-epigallocatechin-3-O-gallate, as judged by its retention time.

7-O-(4-O-α-D-glucopyranosyl-α-D-glucopyranosyl)-(−)-epigallocatechin-3-O-gallate: m/z 783.2, NMR δ ppm (CD$_3$OD); 2.88 (1H, dd), 2.01 (1H, dd), 3.26 (1H, t), 3.46 (1H, dd), 3.6-3.9 (9H, m), 4.08 (1H, t), 5.00 (1H, s), 5.20 (1H, d), 5.43 (1H, d), 5.54 (1H, s), 6.27 (1H, d), 6.34 (1H, d), 6.51 (2H, d), 6.94 (2H, d).

3'-O-α-D-glucopyranosyl-(−)-epigallocatechin-3-O-gallate: m/z 621.1, δ ppm (CD3OD); 2.88 (1H, dd), 2.99 (1H, dd), 3.42 (1H, dd), 3.51 (1H, t), 3.69 (1H, m), 3.8-3.9 (3H, m), 4.88 (1H, d), 4.98 (1H, s), 5.49 (1H, broad s), 5.95 (1H, d), 5.96 (1H, d), 6.65 (1H, d), 7.01 (2H, s), 7.11 (1H, d).

3'-O-(4-O-α-D-glucopyranosyl-α-D-glucopyranosyl)-(−)-epigallocatechin-3-O-gallate: m/z 783.2, δ ppm (CD3OD); 2.87 (1H, broad d), 2.99 (1H, dd), 3.27 (1H, t), 3.44-3.48 (2H, m), 3.6-3.8 (4H, m), 3.85 (2H, d), 3.98 (1H, dd), 4.06 (H, t), 4.85 (1H, d), 4.99 (1H, s), 5.28 (1H, d), 5.49 (1H, broad s), 5.94 (1H, d), 5.96 (1H, d), 6.64 (1H, d), 7.01 (2H, s), 7.09 (1H, d).

9. Expression of His-tagged TRa2 Protein (TRa2-his): Construction of TRa2-his Expression Plasmid and Obtaining of Transformed Yeast To express a C-terminally His-tagged TRa2 protein in yeast cells, the following primer was designed.

TRa2His XhoI-r2: Gctcgagttagtggtggtggtggtggtgtgaagacagcagcaa (SEQ ID NO: 27)

The plasmid pCRTRa2-cDNA was used as a template to perform PCR reaction with primers TraEcoRI-f2 and TRa2His XhoI-r2. PCR was accomplished by using Ex Taq (Takara Bio Inc., Japan) under the following conditions: 94° C. for 2 minutes, (94° C. for 1 minute, 58° C. for 1 minute, 72° C. for 2 minutes)×25 cycles, and 72° C. for 10 minutes. The resulting PCR products were analyzed by agarose gel electrophoresis, confirming a DNA fragment of approximately 1.5 kb. This DNA fragment was excised from the agarose gel and purified by GFX. The resulting DNA fragment was cloned with a TOPO-TA cloning kit (Invitrogen), confirmed for its nucleotide sequence, and designated as plasmid pCR-TRa2-cDNA-His. pCRTRa2-cDNA-His was digested with EcoRI and XhoI to give a DNA fragment of approximately 1.5 kb, which was then ligated to an EcoRI- and SalI-digested fragment of plasmid pYE22m using ligation high (Toyobo Co., Ltd., Japan) to thereby obtain plasmid pYE-TRa2-His. The plasmid pYE-TRa2-His was used to transform yeast S.

cerevisiae strain EH1315. The resulting transformed strain was designated as strain TRa2-3.

Culturing

The strain TRa2-3 was cultured in 20 ml SD(-Trp) at 30° C. for 16 hr. The pre-cultured solution was inoculated into 1 L of SD(-Trp)+100 mM $KH_2PO_4$—KOH (pH 6.0) and cultured at 30° C. for 3 days, followed by centrifugation to collect the culture supernatant.

Purification

The culture supernatant was applied onto a $Ni^{2+}$-chelated Chelating Sepharose Fast Flow (5 ml, Pharmacia Biotech) column equilibrated with Buffer S1 [20 mM $NaH_2PO_4$—NaOH (pH 7.4), 10 mM imidazole, 0.5 M NaCl, 15 mM 2-mercaptoethanol], followed by washing with the same buffer (40 ml). Subsequently, proteins bound to the column were eluted with Buffer E1 [20 mM $NaH_2PO_4$—NaOH (pH 7.4), 200 mM imidazole, 0.5 M NaCl, 15 mM 2-mercaptoethanol]. Active fractions were collected, and then desalted and concentrated using a VIVASPIN (30,000 MWCO, VIVASCIENCE).

Subsequently, the enzyme solution was applied (1.5 ml/min) onto a Resource Q (1 ml, Pharmacia Biotech) column equilibrated with Buffer S2 [20 mM $KH_2PO_4$—KOH (pH 7.4), 15 mM 2-mercaptoethanol, 0.1% CHAPS], followed by washing with the same buffer (10 ml). Subsequently, proteins bound to the column were eluted with a 0-100% linear gradient of Buffer E2 [20 mM $KH_2PO_4$—KOH (pH 7.4), 0.6 M NaCl, 15 mM 2-mercaptoethanol, 0.1% CHAPS] (60 ml). Active fractions were collected, and then desalted and concentrated using a VIVASPIN (30,000 MWCO, VIVASCIENCE).

The same procedure was repeated again to perform Resource Q column chromatography. Active fractions showing a single band on SDS-PAGE were collected, and then desalted and concentrated using a VIVASPIN (30,000 MWCO, VIVASCIENCE).

Measurement of Enzyme Activity:
Glycosylation Activity

A reaction solution (100 μl, 10 mM epigallocatechin-3-O-gallate, 10 mg dextrin, 100 mM Acetate-NaOH (pH 5.3), enzyme solution) was stirred at 45° C. for 24 hr, followed by addition of 0.5% TFA (100 μl) to stop the reaction. After stopping the reaction, the sample was centrifuged to collect the supernatant. The product was analyzed by HPLC under the conditions as shown below, thereby confirming the generation of epigallocatechin-3-O-gallate glycosides. HPLC conditions: Eluent A, 0.1% TFA; Eluent B, 90% acetonitrile, 0.08% TFA; analytical column, Devolosil C30-UG-5 (4.6× 150 mm, NOMURA CHEMICAL); flow rate, 1 ml/min; separation mode, 0 min-5% B, 20 min-50% B, 20.5 min-5% B, 25 min-5% B Example 5

Sugar Selectivity and Sugar Chain Length Specificity

Glycosyl Donor Selectivity 1:

(+)-Catechin (6 mg) was mixed with Cellulase "Onozuka" RS (20 mg), each glycosyl donor (20 mg) and 0.1 M acetate buffer (200 μl, pH 5), followed by stirring at 50° C. for 1 day. After the reaction, the centrifuged supernatant was diluted 10-fold and analyzed by HPLC. The glycosyl donors used were cellobiose (Sigma), dextran (Sigma), maltose (Nacalai Tesque, Inc., Japan), carboxymethylcellulose sodium (Nacalai Tesque, Inc., Japan), soluble starch (Nacalai Tesque, Inc., Japan), dextrin (Nacalai Tesque, Inc., Japan), isomaltooligosaccharide (Wako Pure Chemical Industries, Ltd., Japan), α-cyclodextrin (Wako Pure Chemical Industries, Ltd., Japan), γ-cyclodextrin (Wako Pure Chemical Industries, Ltd., Japan) and trehalose dihydrate (Nacalai Tesque, Inc., Japan).

TABLE 2

| Glycosyl donor | Product (% area) | |
|---|---|---|
| | 7-Glc | 5-Glc |
| Maltose | — | — |
| Cellobiose | — | — |
| Isomaltose | — | — |
| CM-cellulose | — | — |
| Soluble starch | 1.11 | 6.09 |
| Trehalose | — | — |
| Dextrin | 3.14 | 9.47 |
| α-Cyclodextrin | — | — |
| γ-Cyclodextrin | 5.91 | 14.69 |
| Dextran | — | — |
| None | — | — |

This enzyme was found to act on soluble starch, dextrin and γ-cyclodextrin to generate catechin glycosides, but did not act on the other sugars.

Glycosyl Donor Selectivity 2:

(+)-Catechin (3 mg) was mixed with Cellulase "Onozuka" RS (10 mg), each glycosyl donor (10 mg) and 0.1 M acetate buffer (100 μl, pH 5), followed by stirring at 50° C. for 1 day. The glycosyl donors used were maltose, maltotriose, maltotetraose, maltopentaose, maltohexaose, maltoheptaose and dextrin (Nacalai Tesque, Inc., Japan), as well as γ-cyclodextrin (Wako Pure Chemical Industries, Ltd., Japan). After the reaction, the centrifuged supernatant was diluted 10-fold and analyzed by HPLC.

The results obtained are shown in the table below.

TABLE 3

| Glycosyl donor | Product (% area) | |
|---|---|---|
| | 7-Glc | 5-Glc |
| Maltose | — | — |
| Maltotriose | 0.51 | 2.54 |
| Maltotetraose | 1.60 | 7.15 |
| Maltopentaose | 1.98 | 7.87 |
| Maltohexaose | 2.06 | 7.89 |
| Maltoheptaose | 1.97 | 7.39 |
| Dextrin | 2.15 | 8.80 |
| γ-Cyclodextrin | 4.73 | 14.53 |

Example 6

Substrate Specificity

Figure 8:
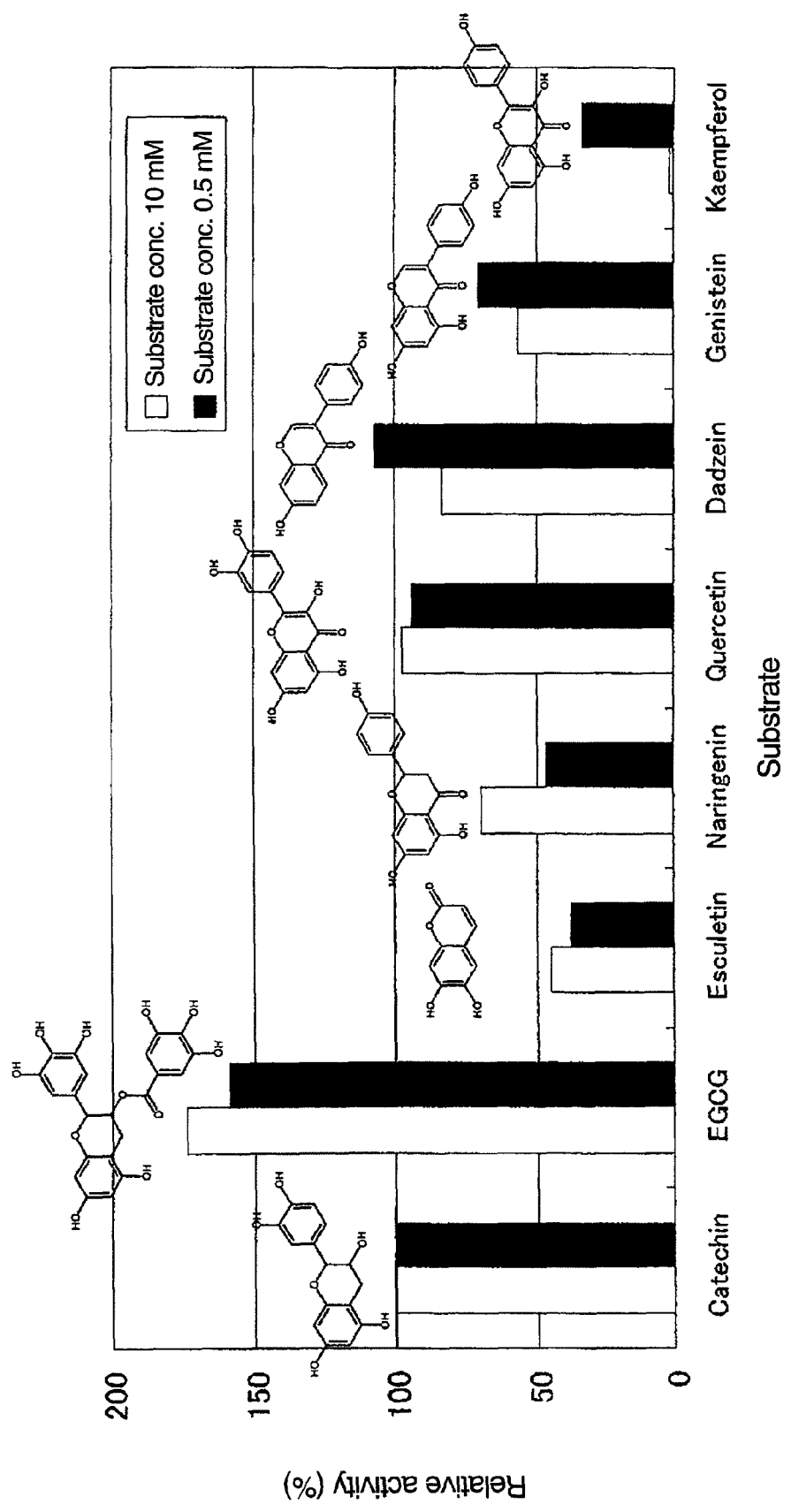
FIG. 8 is a graph showing glycosylation activity of a crude TRa2 enzyme solution prepared from the culture supernatant of a transformant (strain TRa2-1), when used for reaction between each glycosyl acceptor compound ((+)-catechin, (−)-epigallocatechin-3-O-gallate, esculetin, naringenin, quercetin, daidzein, genistein or kaempferol) and dextrin.

The strain TRa2-1 was cultured overnight at 30° C. with shaking in 10 ml YPD medium. After reaching the resting phase, the culture solution was inoculated into the same medium (2% (v/v)) and cultured with shaking at 30° C. for 3 days. After culturing, the supernatant was collected by centrifugation and concentrated 5-fold to give a crude enzyme solution of TRa2. The reaction was performed at 45° C. for 24 hr in 100 μl enzyme reaction solution containing 0.5 mM or 10 mM glycosyl acceptor compound ((+)-catechin, (−)-epigallocatechin-3-O-gallate, esculetin, naringenin, quercetin, daidzein, genistein or kaempferol), 10 mg dextrin, 100 mM acetate buffer (pH 5.2) and the crude enzyme solution, followed by HPLC analysis. The results obtained are shown in FIG. 8.

The area ratio (%) between acceptor compound and glycoside product was 10% for (+)-catechin, 17.7% for (−)-epigallocatechin-3-O-gallate, 3.5% for esculetin, 4.4% for naringenin, 9.4% for quercetin, 10.7% for daidzein, 6.8% for genistein, and 3.1% for kaempferol.

Example 7

Figure 9:
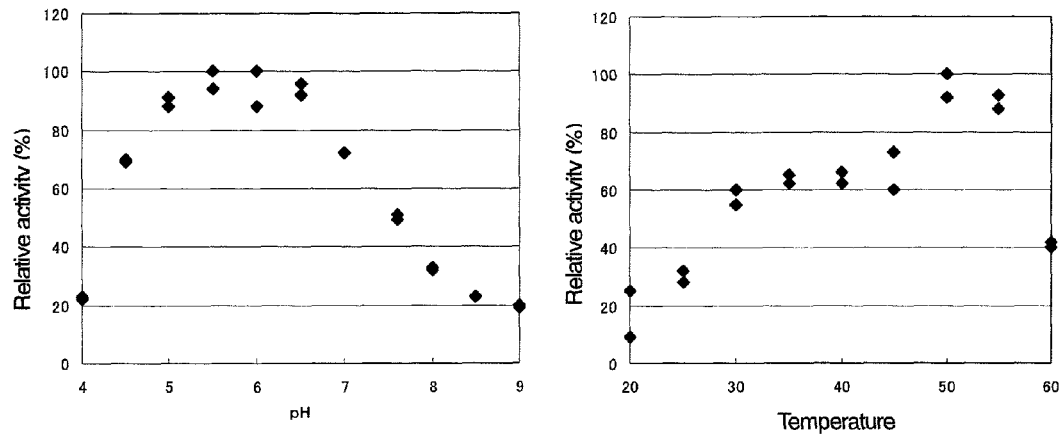
FIG. 9 is graphs showing the optimum pH and optimum temperature during glycosylation reaction with an enzymatic agent.

Study on Optimum pH and Temperature (+)-Catechin (6 mg) was mixed with Pancellase BR (20 mg, Yakult Pharmaceutical Industry Co., Ltd., Japan), dextrin (20 mg, Nacalai Tesque, Inc., Japan) and each buffer (200 μl), followed by stirring at 50° C. for 6 hours. The buffers used were 0.1 M acetate buffer (pH 4 to 5.5), 0.1 M phosphate buffer (pH 6 to 7), and 0.1 M Tris-HCl buffer (pH 7.6 to 9). After the reaction, the centrifuged supernatant was diluted 10-fold and analyzed by HPLC. The results obtained are shown in FIG. 9 (left).

(+)-Catechin (6 mg) and dextrin (20 mg, Nacalai Tesque, Inc., Japan) were dissolved at 50° C. in 200 μl of 0.1 M acetate buffer (pH 5). After cooling, this solution was mixed with Pancellase BR (20 mg, Yakult Pharmaceutical Industry Co., Ltd., Japan) and stirred at 20° C. to 60° C. for 6 hours. After the reaction, the centrifuged supernatant was diluted 10-fold and analyzed by HPLC. The results obtained are shown in FIG. 9 (right).

Example 8

Heat Stability of Glycoside

Figure 10:
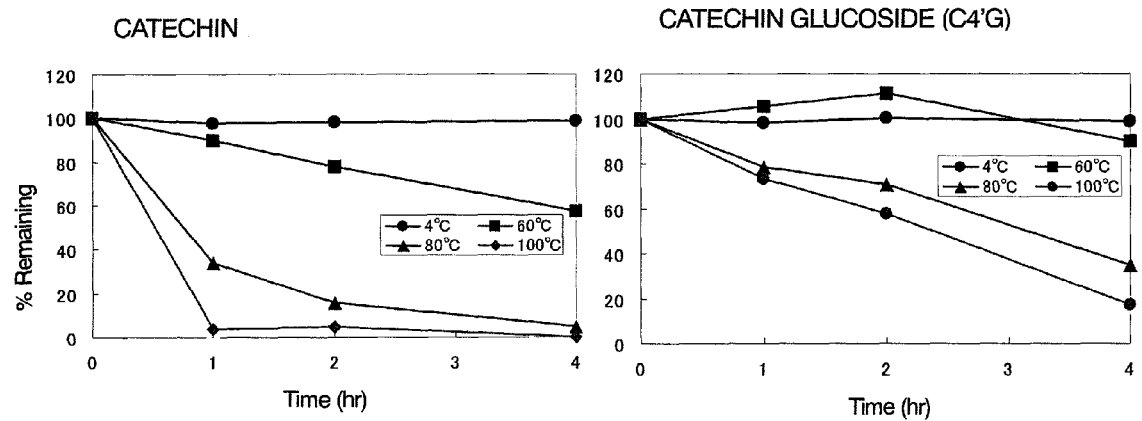
FIG. 10 is a graph showing the % remaining of (+)-catechin or 4'-O-α-D-glucopyranosyl-(+)-catechin after a solution containing the same was treated at different temperatures ranging from 4° C. to 100° C. for 0 to 4 hours.

After 10 mM potassium phosphate buffer (pH 7.0, 30 μl) containing 100 μM (+)-catechin or 4'-O-α-D-glucopyranosyl-(+)—catechin obtained in Example 4 was treated at different temperatures ranging from 4° C. to 100° C. for 0 to 4 hours, each sample was transferred on ice and mixed with 0.1% TFA (60 μl), followed by HPLC analysis in the same manner as shown in Example 1. FIG. 10 shows the % remaining of (+)-catechin or 4'-O-α-D-glucopyranosyl-(+)-catechin when treated at different temperatures. The results indicated that 4'-O-α-D-glucopyranosyl-(+)-catechin was more stable against heat than catechin.

Example 9

Figure 11:
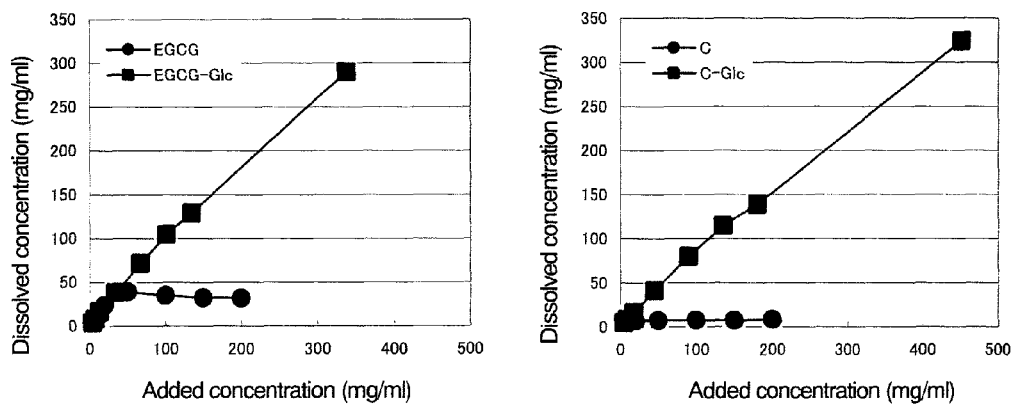
FIG. 11 is a graph showing the water solubility of (+)-catechin and a glycoside thereof or (−)-epigallocatechin-3-O-gallate and a glycoside thereof.

Solubility of Glycoside (+)-Catechin or 5-O-α-D-glucopyranosyl-(+)-catechin obtained in Example 3 was added to water at different concentrations ranging from 10 to 450 mg/ml and dissolved by vigorous stirring, followed by centrifugation to remove precipitates. The supernatant was analyzed by HPLC to quantify the amounts of (+)-catechin and 5-O-α-D-glucopyranosyl-(+)-catechin. The same procedure was also repeated to study the solubility of (−)-epigallocatechin-3-β-gallate or 5-O-α-D-glucopyranosyl-(−)-epigallocatechin-3-O-gallate. The results obtained are shown in FIG. 11.

The results indicated that (+)-catechin was substantially insoluble in water, whereas 5-O-α-D-glucopyranosyl-(+)-catechin showed at least 40-fold or higher solubility. Likewise, (−)-epigallocatechin-3-O-gallate was also confirmed to have significantly increased solubility upon glycosylation.

Example 10

Preparation of Immobilized Enzyme

The following resins were studied as immobilization resins: Express-Ion D (Whatman), Diaion FPHA13 (Mitsubishi Chemical Corporation, Japan), DEAE-Toyopearl 650M (Tosoh Corporation, Japan), DEAE-sepharose CL4B (Amersham Biosciences) and Amberlite IRA904 (Organo). First, Cellulase RS (240 mg) was dissolved in distilled water (8 ml) and each resin (5 ml) was added thereto. After stirring for 30 minutes, the resin was washed twice with distilled water and then lyophilized for use as an immobilized enzyme. Each of the immobilized enzymes (5 ml) was filled into a column (12×150 mm) and circulated with catechin (450 mg), dextrin (1500 mg) and 0.1 M acetate buffer (15 ml, pH 5) to cause a reaction at 50° C. for 4 days. After the reaction, the reaction solution was diluted 10-fold and analyzed by HPLC. The results obtained are shown in Table 4.

TABLE 4

| Immobilization resin | Yield of glycoside (% area) |
| --- | --- |
| Express-Ion D | 15.3 |
| FPHA13 | 25.4 |
| DEAE650M | 18.0 |
| DEAECL4B | 18.3 |
| IRA904 | 11.2 |

Example 11

Figure 12:
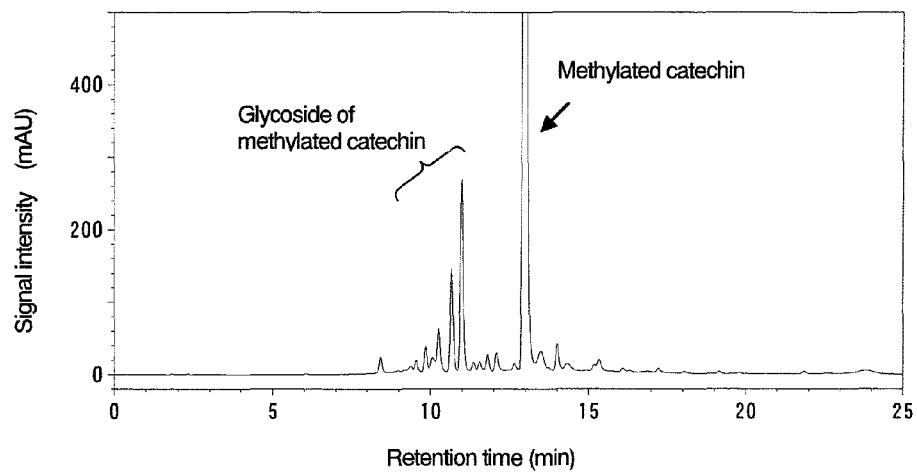
FIG. 12 shows a HPLC analysis chart of the reaction solution when (−)-epigallocatechin-3-(3"-O-methyl)gallate, dextrin and an enzymatic agent were mixed and reacted.

Glycosylation of Methylated Catechin (−)-Epigallocatechin-3-(3"-O-methyl)gallate (2.7 mg) was mixed with Pancellase BR (9 mg), dextrin (9 mg) and 0.1 M acetate buffer (90 μl, pH 5), followed by stirring at 50° C. for 18 hours. After the reaction, the centrifuged supernatant was diluted 10-fold and analyzed by HPLC. The results obtained are shown in FIG. 12.

Example 12

Glycosylation Through Combined Use of Enzymatic Agents

A green tea extract rich in (−)-epigallocatechin-3-O-gallate (30 g, trade name: Teavigo, DSM Nutrition Japan) was mixed with Pancellase BR (100 g), cluster dextrin (100 g, Ezaki Glico Co., Ltd., Japan), α-cyclodextrin (100 g) and cyclodextrin glucanotransferase (100 ml, Amano Enzyme Inc., Japan) in 0.1 M acetate buffer (1000 ml, pH 5), followed by stirring at 50° C. for 3.5 hours. After the reaction, the centrifuged supernatant was adsorbed onto a Sepharose LH20 (1000 ml, Amersham Biosciences) column. The column was washed with distilled water (6000 ml) and then eluted stepwise with 30% ethanol (6000 ml), followed by concentration and lyophilization to prepare a glycoside fraction (13.9 g).

Example 13

Taste Evaluation of Glycosides

Figure 13:
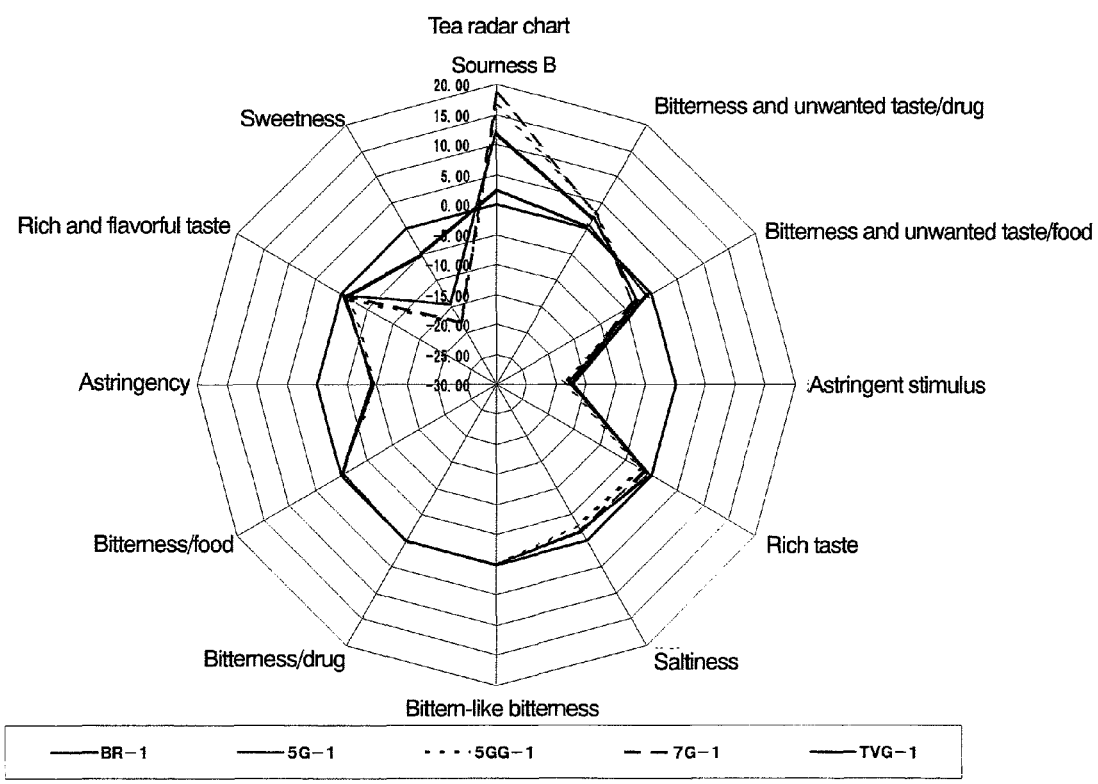
FIG. 13 shows a radar chart of taste quality obtained with a taste sensor for a green tea extract rich in (−)-epigallocatechin-3-O-gallate (TVG-1), a glycoside fraction thereof (BR-1), and uniformly-purified products of individual glycosides contained in BR-1 (i.e., 5-O-α-D-glucopyranosyl-(−)-epigallocatechin-3-O-gallate (5G-1), 5-O-(4-O-α-D-glucopyranosyl-α-D-glucopyranosyl)-(−)-epigallocatechin-3-O-gallate (5GG-1), and 7-O-α-D-glucopyranosyl-(−)-epigallocatechin-3-O-gallate (7G-1)).

The glycoside prepared in Example 12 (BR-1), individual glycoside components uniformly purified (i.e., 5-O-α-D-glucopyranosyl-(−)-epigallocatechin-3-O-gallate (5G-1), 5-O-(4-O-α-D-glucopyranosyl-α-D-glucopyranosyl)-(−)-epigallocatechin-3-O-gallate (5GG-1) and 7-O-α-D-glucopyranosyl-(−)-epigallocatechin-3-O-gallate (7G-1)) and the green tea extract (TVG-1) used as a source material were each dissolved at 200 ppm in distilled water and evaluated for taste quality by using a taste sensor (Taste & Aroma Strategic Research Institute Co., Ltd., Japan) which detects the intensity of each taste as a potential difference in an "artificial lipid membrane" electrode mimicking the human tongue. The results obtained are shown in FIG. 13. The tested glycosides each showed a significantly lower level of astringent taste than the green tea extract (TVG-1) serving as a control, indicating that the taste quality was improved through glycosylation. Likewise, sensory tests made by panelists also provided the evaluation results indicating reduced bitter and astringent tastes and hence increased drinkability.

The invention claimed is:

1. A compound represented by the following formula:

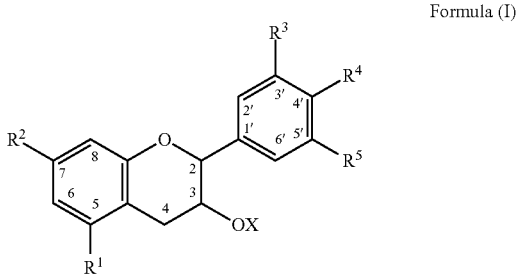

Formula (I)

wherein at least one of $R^1$ to $R^4$ represents an α-linked glucose residue or maltose residue or maltooligosaccharide residue, and each of the others represents OH;

$R^5$ represents OH or H; and

X represents H or a galloyl group, provided that the following compounds are excluded:

a compound in which $R^1$ represents glucose, $R^2$-$R^4$ represent OH, and $R^5$ and X represent H;

a compound in which $R^2$ represents glucose, $R^1$ and $R^3$-$R^4$ represent OH, and $R^5$ and X represent H;

a compound in which $R^4$ represents glucose, $R^1$-$R^3$ represent OH, and $R^5$ and represent H;

a compound in which $R^2$ represents maltose, $R^1$ and $R^3$-$R^4$ represent OH, and $R^5$ and X represent H;

a compound in which $R^3$ represents glucose, $R^1$-$R^2$ and $R^4$ represent OH, and $R^5$ and X represent H;

a compound in which $R^1$ represents maltose, $R^2$-$R^4$ represent OH, and $R^5$ and X represent H;

a compound in which $R^3$ represents glucose, $R^1$-$R^2$ and $R^4$ represent OH, and $R^5$ and X represent H;

a compound in which $R^3$ represents glucose, $R^1$-$R^2$ and $R^4$-$R^5$ represent OH, and X represents H;

a compound in which $R^2$-$R^3$ represent glucose, $R^1$ and $R^4$-$R^5$ represent OH, and X represents H;

a compound in which $R^1$ and $R^3$ represent glucose, $R^2$ and $R^4$-$R^5$ represent OH, and X represents H;

a compound in which $R^3$ represents glucose, $R^1$-$R^2$ and $R^4$-$R^5$ represent OH, and X represents H;

a compound in which $R^4$ represents glucose, $R^1$-$R^3$ and $R^5$ represent OH, and X represents H;

a compound in which $R^3$ represents glucose, $R^1$-$R^2$ and $R^4$ represent OH, $R^5$ represents H, and X represents a galloyl group;

a compound in which $R^2$-$R^3$ represent glucose, $R^1$ and $R^4$-$R^5$ represent OH, and X represents a galloyl group;

a compound in which $R^3$ represents glucose, $R^1$-$R^2$ and $R^4$-$R^5$ represent OH, and X represents a galloyl group;

a compound in which $R^4$ represents glucose, $R^1$-$R^3$ and $R^5$ represent OH, and X represents a galloyl group;

a compound in which $R^4$ represents glucose, $R^1$-$R^3$ represent OH, $R^5$ represents H, and X represents a galloyl group;

a compound in which $R^2$ represents glucose, $R^1$ and $R^3$-$R^5$ represent OH, and X represents a galloyl group;

a compound in which $R^2$ and $R^4$ represent glucose, $R^1$, $R^3$, and $R^5$ represent OH, and X represents a galloyl group;

a compound in which $R^2$-$R^3$ represent glucose, $R^1$ and $R^4$ represent OH, and $R^5$ and X represent H;

a compound in which $R^1$ and $R^3$ represent glucose, $R^2$ and $R^4$ represent OH, and $R^5$ and X represent H;

a compound in which $R^3$-$R^4$ represent glucose, $R^1$-$R^2$ represent OH, and $R^5$ and X represent H;

a compound in which $R^1$ and $R^4$ represent glucose, $R^2$-$R^3$ represent OH, and $R^5$ and X represent H;

a compound in which $R^2$ and $R^4$ represent glucose, $R^1$, $R^3$, and $R^5$ represent OH, and X represents H; and a compound in which $R^2$ and $R^4$ represent glucose, $R^1$ and $R^3$ represent OH, and $R^5$ and X represent H.

2. The compound according to claim 1, which is selected from the group consisting of:

5-O-α-D-glucopyranosyl-(−)-epigallocatechin-3-O-gallate;

7-O-(4-O-α-D-glucopyranosyl-α-D-glucopyranosyl)-(−)-epigallocatechin-3-O-gallate;

4'-O-(4-O-α-D-glucopyranosyl-α-D-glucopyranosyl)-(+)-catechin;

3'-O-(4-O-α-D-glucopyranosyl-α-D-glucopyranosyl)-(+)-catechin; and

3'-O-(4-O-α-D-glucopyranosyl-α-D-glucopyranosyl)-(−)-epigallocatechin-3-O-gallate.

3. A food, pharmaceutical or cosmetic composition, which comprises the compound according to claim 1.

4. A beverage, which comprises the composition according to claim 3.

5. A compound represented by the following formula:

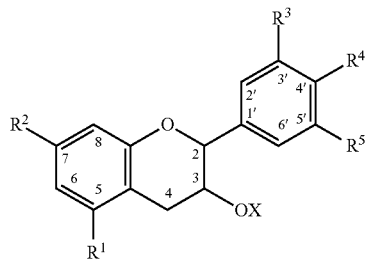

wherein
at least one of $R^1$, $R^2$, and $R^4$ represents an α-linked glucose residue or maltose residue or maltooligosaccharide residue, and each of the others represents OH;
$R^3$ represents a maltose residue;
$R^5$ represents OH or H; and
X represents H or a galloyl group.

6. A glycoside of a flavonoid compound selected from the following:

5-O-α-D-glucopyranosyl-(−)-epigallocatechin-3-O-gallate;

3'-O-(4-O-α-D-glucopyranosyl-α-D-glucopyranosyl)-(+)-catechin; and

3'-O-(4-O-α-D-glucopyranosyl-α-D-glucopyranosyl)-(−)-epigallocatechin-3-O-gallate.

7. A food, pharmaceutical or cosmetic composition, which comprises the compound according to claim 2.

8. A beverage, which comprises the composition according to claim 7.

* * * * *

```
                        SEQUENCE LISTING

<160> NUMBER OF SEQ ID NOS: 33

<210> SEQ ID NO 1
<211> LENGTH: 26
<212> TYPE: DNA
<213> ORGANISM: Unknown
<220> FEATURE:
<223> OTHER INFORMATION: Description of Unknown: Ascomycetes
      sequence
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 1
taytgyggng gnacnttyaa rggnyt                                         26

<210> SEQ ID NO 2
<211> LENGTH: 26
<212> TYPE: DNA
<213> ORGANISM: Unknown
<220> FEATURE:
<223> OTHER INFORMATION: Description of Unknown: Ascomycetes
      sequence
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 2
ttytcnacrt gyttnacngt rtcdat                                         26

<210> SEQ ID NO 3
<211> LENGTH: 27
<212> TYPE: DNA
<213> ORGANISM: Unknown
<220> FEATURE:
<223> OTHER INFORMATION: Description of Unknown: Ascomycetes
      sequence
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (13)..(13)
```

-continued

```
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 3
ggtnayrtcy tcnckrttng cnggrtc                                        27

<210> SEQ ID NO 4
<211> LENGTH: 20
<212> TYPE: DNA
<213> ORGANISM: Trichoderma viride
<220> FEATURE:
<223> OTHER INFORMATION: Strain IAM5141

<400> SEQUENCE: 4
ccaacctggt atctacatac                                                20

<210> SEQ ID NO 5
<211> LENGTH: 19
<212> TYPE: DNA
<213> ORGANISM: Trichoderma viride
<220> FEATURE:
<223> OTHER INFORMATION: Strain IAM5141

<400> SEQUENCE: 5
agatggcatc aaatcccat                                                 19

<210> SEQ ID NO 6
<211> LENGTH: 2633
<212> TYPE: DNA
<213> ORGANISM: Trichoderma viride
<220> FEATURE:
<223> OTHER INFORMATION: Strain IAM5141

<400> SEQUENCE: 6
tcatacaaag ctatttcgaa gaccaatatt ctaccccctt ctccgacgat agagccctat     60
ggtaatgggc cgatgggttg cttattcggc cctttgtcgg ccggggcatg cgtgtttgac    120
atgttgaagc ttgggcagat ctgggatcgg cgtcacggga tgcctataac aggaggtctg    180
taagtggctg tttggccgcg gcaagtttta ttgccggagc gaatatggcg tctcaatgcg    240
ctacgggatc ttgttttttgg tctgtttggt gtcgtttggg caaggggggc atatgcgata   300
tctatgccct tggggatata tatatatggc ttgccgctct ctcttccttg gatcagcttg    360
ctgaccacag acctcttgca gacgcagcct gaactcgagc atcccacagc tgaaagaaga    420
agatgaagct tcgatccgcc gtcccgctgc tgttgcagct ttctctcccg gccgtccttg    480
gcgccgacac ggcagactgg aggtctcgta ccatctactt tgccctgaca gaccgaattg    540
ctcgcagctc aagcgacacg ggaggctctg cgtgtacaaa tctgaatgac tactgtggtg    600
gcacgttcca gggcttggag agcaagctgg actacatcaa gggcatggga tttgatgcca    660
tctggatcaa ccccgtcgta accagtgagt tgcccatcta tccccatcct cttgattggt    720
ggctaacatc tcttgaaaga cagtgatttc ggcttccatg ctactgggc  actggatcta    780 aacactatca attctcacta tggcactgcg gatgatttaa agagtctcgt tgatgctgca    840
catggcaagg tatattcaca ccattctccc aactgctgag tgtcagtgct agaaataacc    900
aaaaacaggg cttctacatg atggtcgacg ttgtagccaa ccacatggga aacgcaaaca    960
```

```
tcacagacga ctccccctcc cctctgaacc aacaatcctc ataccacaca aaatgtgaca    1020
ttgacttcaa caaccagacc agcgtcgaaa actgttggct tgctggcctc ccagacgttg    1080
acacccagga ccctaccatc aggagcctct accaggactg ggtgtccaac ctggtatcta    1140
catacggctt cgacggcgtc cgcatcgaca ccgtcaggca cgtcgagcag gactactggc    1200
ccggcttcgt caatgccagc ggcgtgtact gcatcggcga agtcttcaac ggagacccag    1260
actttatgca gccctaccaa tcgctcatgc ccggcctcct caactacgcc atcttctacc    1320
ccctcaacgc cttttatcag cagacgggct cctcccaagc cctggtcgac atgcatgacc    1380
gtctcagctc gttcccagac ccgacggcgc tgggcacctt tgtcgataac cacgacaacc    1440
cccgcttcct cagcgtcaag aacgacacgt ctctcttcaa gaatgccctg acctacacca    1500
ttctcggccg aggcatcccc attgtctact acggctccga gcaagccttt cgggaagca    1560 acgaccccgc caacagagag gacctctggc gcagcggcta caacaccgag acggacatgt    1620
acaatgccat ctccaagctc acctttgcca agcacacggc cggcgccctc gccgacaacg    1680
accacaagca cctgtacgtc gagcccacgg catacgcctg gagccgcgcc ggcggcaagc    1740
tggtggcctt taccaccaac agcggcggcg gcagctcggc ccagttctgc ttcggcacgc    1800
aggtccccaa cgggagctgg acgaatgtgt tgatggcgg caatggcccg acgtacactg    1860
ctgatggcaa tggacagctc tgcttgacca cgacgaatgg tgagccgatt gtgctgctgt    1920
cttcataaaa caatatggcg acatataata tacatgtata tcacctagta catacttgga    1980
taggtacgtg ttacttaccc ggatagagct tcatgttgtt accttcaagc tgttgtttct    2040
ttcttctctc ttttgtggac atactgtacg atcatgaagg gtacatattt tagtcgtaac    2100
aaaattaggc atttactact acctagacta aactgtttgt tgttgatcat gtacctagag    2160
caagcaatga accatgccat gatttccttc atctcccaga cccgtatttg aattgcctgt    2220
ggatagatgt gcttgaaaga cctgccatgc gctcaaagta attgttattg aatagtccgt    2280
cccaaaatat taactgcagt gccgagatat ctgttgttcc gtcaggcctg ttcaacctgc    2340
ggggatagaa aatctccatg tgctcatgag tgcataaatt ccgcaccgaa tcctccgctt    2400
ccaaaaaaaa aaaagaagca atattataaa aagcaaagtc gtcatgccgt caaatagcct    2460
ttatagtccc gtgtatgctc gcaagtcttg tccgtcgtcg ttagcctgta ttattcacat    2520
gcgtgtgtca tcgatagcct tgtgtttctc gtgtcgcacg atttgctctt gatattgacc    2580
acattccttc ggtacaatga gcaaatatat ataccgttgt ggtgggtaat gag          2633
```

<210> SEQ ID NO 7
<211> LENGTH: 30
<212> TYPE: DNA
<213> ORGANISM: Trichoderma viride
<220> FEATURE:
<223> OTHER INFORMATION: Strain IAM5141

<400> SEQUENCE: 7

```
ggaattcatg aagcttcgat ccgccgtccc                                       30
```

<210> SEQ ID NO 8
<211> LENGTH: 30
<212> TYPE: DNA
<213> ORGANISM: Trichoderma viride
<220> FEATURE:
<223> OTHER INFORMATION: Strain IAM5141

<400> SEQUENCE: 8
ccgctcgagt tatgaagaca gcagcacaat    30

<210> SEQ ID NO 9
<211> LENGTH: 1392
<212> TYPE: DNA
<213> ORGANISM: Trichoderma viride
<220> FEATURE:
<223> OTHER INFORMATION: Strain IAM5141
<220> FEATURE:
<221> NAME/KEY: CDS
<222> LOCATION: (1)..(1389)

<400> SEQUENCE: 9

```
atg aag ctt cga tcc gcc gtc ccg ctg ctg ttg cag ctt tct ctc ccg      48
Met Lys Leu Arg Ser Ala Val Pro Leu Leu Leu Gln Leu Ser Leu Pro
 1               5                  10                  15 gcc gtc ctt ggc gcc gac acg gca gac tgg agg tct cgt acc atc tac      96
Ala Val Leu Gly Ala Asp Thr Ala Asp Trp Arg Ser Arg Thr Ile Tyr
             20                  25                  30 ttt gcc ctg aca gac cga att gct cgc agc tca agc gac acg gga ggc     144
Phe Ala Leu Thr Asp Arg Ile Ala Arg Ser Ser Ser Asp Thr Gly Gly
         35                  40                  45 tct gcg tgt aca aat ctg aat gac tac tgt ggt ggc acg ttc cag ggc     192
Ser Ala Cys Thr Asn Leu Asn Asp Tyr Cys Gly Gly Thr Phe Gln Gly
     50                  55                  60 ttg gag agc aag ctg gac tac atc aag ggc atg gga ttt gat gcc atc     240
Leu Glu Ser Lys Leu Asp Tyr Ile Lys Gly Met Gly Phe Asp Ala Ile
 65                  70                  75                  80 tgg atc aac ccc gtc gta acc aac agt gat ttc ggc ttc cat ggc tac     288
Trp Ile Asn Pro Val Val Thr Asn Ser Asp Phe Gly Phe His Gly Tyr
                 85                  90                  95 tgg gca ctg gat cta aac act atc aat tct cac tat ggc act gcg gat     336
Trp Ala Leu Asp Leu Asn Thr Ile Asn Ser His Tyr Gly Thr Ala Asp
            100                 105                 110 gat tta aag agt ctc gtt gat gct gca cat ggc aag ggc ttc tac atg     384
Asp Leu Lys Ser Leu Val Asp Ala Ala His Gly Lys Gly Phe Tyr Met
        115                 120                 125 atg gtc gac gtt gta gcc aac cac atg gga aac gca aac atc aca gac     432
Met Val Asp Val Val Ala Asn His Met Gly Asn Ala Asn Ile Thr Asp
    130                 135                 140 gac tcc ccc tcc cct ctg aac caa caa tcc tca tac cac aca aaa tgt     480
Asp Ser Pro Ser Pro Leu Asn Gln Gln Ser Ser Tyr His Thr Lys Cys
145                 150                 155                 160 gac att gac ttc aac aac cag acc agc gtc gaa aac tgt tgg ctt gct     528
Asp Ile Asp Phe Asn Asn Gln Thr Ser Val Glu Asn Cys Trp Leu Ala
                165                 170                 175 ggc ctc cca gac gtt gac acc cag gac cct acc atc agg agc ctc tac     576
Gly Leu Pro Asp Val Asp Thr Gln Asp Pro Thr Ile Arg Ser Leu Tyr
            180                 185                 190 cag gac tgg gtg tcc aac ctg gta tct aca tac ggc ttc gac ggc gtc     624
Gln Asp Trp Val Ser Asn Leu Val Ser Thr Tyr Gly Phe Asp Gly Val
        195                 200                 205 cgc atc gac acc gtc agg cac gtc gag cag gac tac tgg ccc ggc ttc     672
Arg Ile Asp Thr Val Arg His Val Glu Gln Asp Tyr Trp Pro Gly Phe
    210                 215                 220 gtc aat gcc agc ggc gtg tac tgc atc ggc gaa gtc ttc aac gga gac     720
Val Asn Ala Ser Gly Val Tyr Cys Ile Gly Glu Val Phe Asn Gly Asp
225                 230                 235                 240 cca gac ttt atg cag ccc tac caa tcg ctc atg ccc ggc ctc ctc aac     768
Pro Asp Phe Met Gln Pro Tyr Gln Ser Leu Met Pro Gly Leu Leu Asn
                245                 250                 255
```

| | | |
|---|---|---|
| tac gcc atc ttc tac ccc ctc aac gcc ttt tat cag cag acg ggc tcc<br>Tyr Ala Ile Phe Tyr Pro Leu Asn Ala Phe Tyr Gln Gln Thr Gly Ser<br>    260                        265                      270 | | 816 |
| tcc caa gcc ctg gtc gac atg cat gac cgt ctc agc tcg ttc cca gac<br>Ser Gln Ala Leu Val Asp Met His Asp Arg Leu Ser Ser Phe Pro Asp<br>    275                        280                      285 | | 864 |
| ccg acg gcg ctg ggc acc ttt gtc gat aac cac gac aac ccc cgc ttc<br>Pro Thr Ala Leu Gly Thr Phe Val Asp Asn His Asp Asn Pro Arg Phe<br>    290                        295                      300 | | 912 |
| ctc agc gtc aag aac gac acg tct ctc ttc aag aat gcc ctg acc tac<br>Leu Ser Val Lys Asn Asp Thr Ser Leu Phe Lys Asn Ala Leu Thr Tyr<br>305                        310                      315                      320 | | 960 |
| acc att ctc ggc cga ggc atc ccc att gtc tac tac ggc tcc gag caa<br>Thr Ile Leu Gly Arg Gly Ile Pro Ile Val Tyr Tyr Gly Ser Glu Gln<br>                        325                      330                      335 | | 1008 |
| gcc ttt tcg gga agc aac gac ccc gcc aac aga gag gac ctc tgg cgc<br>Ala Phe Ser Gly Ser Asn Asp Pro Ala Asn Arg Glu Asp Leu Trp Arg<br>                340                      345                      350 | | 1056 |
| agc ggc tac aac acc gag acg gac atg tac aat gcc atc tcc aag ctc<br>Ser Gly Tyr Asn Thr Glu Thr Asp Met Tyr Asn Ala Ile Ser Lys Leu<br>              355                      360                      365 | | 1104 |
| acc ttt gcc aag cac acg gcc ggc ggc ctc gcc gac aac gac cac aag<br>Thr Phe Ala Lys His Thr Ala Gly Gly Leu Ala Asp Asn Asp His Lys<br>370                        375                      380 | | 1152 |
| cac ctg tac gtc gag ccc acg gca tac gcc tgg agc cgc gcc ggc ggc<br>His Leu Tyr Val Glu Pro Thr Ala Tyr Ala Trp Ser Arg Ala Gly Gly<br>385                        390                      395                      400 | | 1200 |
| aag ctg gtg gcc ttt acc acc aac agc ggc ggc ggc agc tcg gcc cag<br>Lys Leu Val Ala Phe Thr Thr Asn Ser Gly Gly Gly Ser Ser Ala Gln<br>                        405                      410                      415 | | 1248 |
| ttc tgc ttc ggc acg cag gtc ccc aac ggg agc tgg acg aat gtg ttt<br>Phe Cys Phe Gly Thr Gln Val Pro Asn Gly Ser Trp Thr Asn Val Phe<br>              420                      425                      430 | | 1296 |
| gat ggc ggc aat ggc ccg acg tac act gct gat ggc aat gga cag ctc<br>Asp Gly Gly Asn Gly Pro Thr Tyr Thr Ala Asp Gly Asn Gly Gln Leu<br>              435                      440                      445 | | 1344 |
| tgc ttg acc acg acg aat ggt gag ccg att gtg ctg ctg tct tca taa<br>Cys Leu Thr Thr Thr Asn Gly Glu Pro Ile Val Leu Leu Ser Ser<br>450                        455                      460 | | 1392 |

<210> SEQ ID NO 10
<211> LENGTH: 463
<212> TYPE: PRT
<213> ORGANISM: Trichoderma viride
<220> FEATURE:
<223> OTHER INFORMATION: Strain IAM5141

<400> SEQUENCE: 10

Met Lys Leu Arg Ser Ala Val Pro Leu Leu Leu Gln Leu Ser Leu Pro
1               5                   10                  15

Ala Val Leu Gly Ala Asp Thr Ala Asp Trp Arg Ser Arg Thr Ile Tyr
            20                  25                  30

Phe Ala Leu Thr Asp Arg Ile Ala Arg Ser Ser Ser Asp Thr Gly Gly
        35                  40                  45

Ser Ala Cys Thr Asn Leu Asn Asp Tyr Cys Gly Gly Thr Phe Gln Gly
    50                  55                  60

Leu Glu Ser Lys Leu Asp Tyr Ile Lys Gly Met Gly Phe Asp Ala Ile
65                  70                  75                  80

Trp Ile Asn Pro Val Val Thr Asn Ser Asp Phe Gly Phe His Gly Tyr
                85                  90                  95

Trp Ala Leu Asp Leu Asn Thr Ile Asn Ser His Tyr Gly Thr Ala Asp
            100                 105                 110

Asp Leu Lys Ser Leu Val Asp Ala Ala His Gly Lys Gly Phe Tyr Met
        115                 120                 125

Met Val Asp Val Val Ala Asn His Met Gly Asn Ala Asn Ile Thr Asp
130                 135                 140

Asp Ser Pro Ser Pro Leu Asn Gln Gln Ser Ser Tyr His Thr Lys Cys
145                 150                 155                 160

Asp Ile Asp Phe Asn Asn Gln Thr Ser Val Glu Asn Cys Trp Leu Ala
                165                 170                 175

Gly Leu Pro Asp Val Asp Thr Gln Asp Pro Thr Ile Arg Ser Leu Tyr
            180                 185                 190

Gln Asp Trp Val Ser Asn Leu Val Ser Thr Tyr Gly Phe Asp Gly Val
        195                 200                 205

Arg Ile Asp Thr Val Arg His Val Glu Gln Asp Tyr Trp Pro Gly Phe
210                 215                 220

Val Asn Ala Ser Gly Val Tyr Cys Ile Gly Glu Val Phe Asn Gly Asp
225                 230                 235                 240

Pro Asp Phe Met Gln Pro Tyr Gln Ser Leu Met Pro Gly Leu Leu Asn
                245                 250                 255

Tyr Ala Ile Phe Tyr Pro Leu Asn Ala Phe Tyr Gln Gln Thr Gly Ser
            260                 265                 270

Ser Gln Ala Leu Val Asp Met His Asp Arg Leu Ser Ser Phe Pro Asp
        275                 280                 285

Pro Thr Ala Leu Gly Thr Phe Val Asp Asn His Asp Asn Pro Arg Phe
290                 295                 300

Leu Ser Val Lys Asn Asp Thr Ser Leu Phe Lys Asn Ala Leu Thr Tyr
305                 310                 315                 320

Thr Ile Leu Gly Arg Gly Ile Pro Ile Val Tyr Tyr Gly Ser Glu Gln
                325                 330                 335

Ala Phe Ser Gly Ser Asn Asp Pro Ala Asn Arg Glu Asp Leu Trp Arg
            340                 345                 350

Ser Gly Tyr Asn Thr Glu Thr Asp Met Tyr Asn Ala Ile Ser Lys Leu
        355                 360                 365

Thr Phe Ala Lys His Thr Ala Gly Gly Leu Ala Asp Asn Asp His Lys
370                 375                 380

His Leu Tyr Val Glu Pro Thr Ala Tyr Ala Trp Ser Arg Ala Gly Gly
385                 390                 395                 400

Lys Leu Val Ala Phe Thr Thr Asn Ser Gly Gly Ser Ser Ala Gln
                405                 410                 415

Phe Cys Phe Gly Thr Gln Val Pro Asn Gly Ser Trp Thr Asn Val Phe
            420                 425                 430

Asp Gly Gly Asn Gly Pro Thr Tyr Thr Ala Asp Gly Asn Gly Gln Leu
        435                 440                 445

Cys Leu Thr Thr Thr Asn Gly Glu Pro Ile Val Leu Leu Ser Ser
450                 455                 460

<210> SEQ ID NO 11
<211> LENGTH: 583
<212> TYPE: DNA
<213> ORGANISM: Trichoderma reesei
<220> FEATURE:
<223> OTHER INFORMATION: Strain IFO31328

<400> SEQUENCE: 11

```
tggagagcaa gttggactac atcaagggca tgggatttga tgcaatctgg attacgcctg    60
ttgtgacgag tgagtttcac cttgccttgc cttgcgtcgc acaaagcctt cgggagggaa   120
taggtagctg actctgtgat acccatgggt agacagtgat ggcggctatc atggctactg   180
ggcggaggac attgactcca tcaattccca ttatggctct gcggacgact tgaagagtct   240
tgtcaatgcc gcgcatagca aggtactttc ttcccatcat cacatggctt tacccttttg   300
cgttgttcta aagcgagaga aactagggct tctatatgat ggtggatgtc gtcgccaacc   360
acatgggcta cgccaacatc accgacgata gtcctactcc tctgaaccaa gcctcttcgt   420
atcacccgga gtgtgacatc gactacaaca accagaccag cgtccaggaa tgctggatca   480
gtggtctccc ggatctcgac accgagagcc cgatgatccg cagcctctac caggactggg   540
tctccaacct cgtgtccacg tacggcttcg acggcgtccg cat                     583
```

`<210>` SEQ ID NO 12
`<211>` LENGTH: 592
`<212>` TYPE: DNA
`<213>` ORGANISM: Trichoderma viride
`<220>` FEATURE:
`<223>` OTHER INFORMATION: Strain IFO31327

`<400>` SEQUENCE: 12

```
tggagagcaa gttggactac atcaagggca tgggatccga tgccatctgg atcacacctg    60
ttgtgacgag tgagtctttt cataccttgc cctgccttgc ctcgcctcgc cttgcatgtg   120
tcgcatacag gcttctggta tgcatagcta aacctgatac ctctggacag acagtgatgg   180
gggctaccat ggctattggg cggaggacat cgactccatc aactctcatt atggctctgc   240
ggacgatctc aagagtctcg tcaacgccgc gcatagcaag gtattccctt tgttcacac   300 cagacttcat gattatcaaa attaacacaa accagggctt ctatatgatg gtggacgtcg   360
tggccaacca catgggctac gccaatatct ctgacgatag tccctctcca ctgaaccagg   420
cctcgtcgta tcaccccgag tgtgatatcg actacaacag ccaaaccagc gtcgagaact   480
gctggatcag cggcctcccg gatctcaaca cgcagagctc aaccatccgc agcctctacc   540
aggactgggt ctccaacctc gtgtccacgt acggcttcga cggcgtccgc at           592
```

`<210>` SEQ ID NO 13
`<211>` LENGTH: 583
`<212>` TYPE: DNA
`<213>` ORGANISM: Trichoderma viride
`<220>` FEATURE:
`<223>` OTHER INFORMATION: Strain IFO5720

`<400>` SEQUENCE: 13

```
tggagagcaa gttggactac atcaagggca tgggattcga tgccatctgg atcacgcctg    60
ttgtgacgag tgagtctttg ccctgtcccg ccttgcctcg ggtcgtacat gggctgctag   120
agtgaacagc tgcactgat acctctgaac agacagtgat ggggggctacc atggctattg   180 ggcggaggat ctcgattcca tcaactctca ctacggctct gcggatgact tgaagagtct   240
cgtcaacgcc gcacatagca aggtacttct tcctggcatg atatgacctt cgcctattct   300
cctggttcta atgcgagaca aaccagggct tctatatgat ggtagacgtc gtggccaacc   360
acatgggcta cgccaacatc tccgatgaca gccccccccc tctgaaccag gcctcttcgt   420
atcacgccga gtgtgacatt gactacaaca accagaccag cgtccagaac tgctggatca   480
gcggcctccc tgatctcgac acgcagagcc cgaccatccg cagcctctac caggactggg   540
```

```
tctccgacct cgtgtccacg tacggcttcg acggcgtccg cat                583
```

<210> SEQ ID NO 14
<211> LENGTH: 569
<212> TYPE: DNA
<213> ORGANISM: Trichoderma viride
<220> FEATURE:
<223> OTHER INFORMATION: Strain IFO30498

<400> SEQUENCE: 14

```
tggagagcaa gttggactac atcaagggca tgggattcga tgccatctgg atcaccccg    60 tcgttaccag tgagttgccg acctatcccc agccaatgat atcaattcat cctcttgatt   120
aatagctaac atgccttgaa tagacagcga tttcggatac cacggttact gggctcagga   180
tattaattcc atcaattctc actatggttc ctcggatgat ttaaagagtc ttgttgatgc   240
tgctcatagc aaggtatata tttacacgac actttcaatt ttatgggtct gtgctaaacc   300
aatcaacaac agggcttcta catgatggtc gatgtcgtcg ccaaccatat gggaaacgca   360
aacatcacag acgactctcc ctctcctctg aaccaagact cctcatacca cacaaagtgt   420
gacatcgacy tcaacaacca gaccagcgtc gaaaactgtt ggctcgccgg cctcccggat   480
cttgacactc aaagccctac catcaggagc ttgtaccagg actgggtgtc caaccttgta   540
tctacatacg gcttcgacgg cgtccgcat                                     569
```

<210> SEQ ID NO 15
<211> LENGTH: 592
<212> TYPE: DNA
<213> ORGANISM: Trichoderma reesei
<220> FEATURE:
<223> OTHER INFORMATION: Strain IFO31329

<400> SEQUENCE: 15

```
tggagagcaa gttggactac atcaagggca tgggattcga tgccatctgg atcacacctg    60
ttgtgacgag tgagtctttt catacccttgc cctgccttgc ctcgcctcgc cttgcatgtg   120
tcgcatacag gcttctggta tgcatagcta aacctgatac ctctggacag acagtgatgg   180
gggctaccat ggctattggg cggaggacat cgactccatc aactctcatt atggctctgc   240
ggacgatctc aagagtctcg tcaacgccgc gcatagcaag gtattccctt tgttcacac    300 cagacttcat gattatcaaa attaacacaa accagggctt ctatatgatg gtggacgtcg   360
tggccaacca catgggctac gccaatatct ctgacgatag tccctctcca ctgaaccagg   420
cctcgtcgta tcaccccgag tgtgatatcg actacaacaa ccaaaccagc gtcgagaact   480
gctggatcag cggccyccccg gatctcaaca cgcagagctc aaccatccgc agcctctacc   540
aggactgggt ctccaacctc gtgtccacgt acggcttcga cggcgtccgc at           592
```

<210> SEQ ID NO 16
<211> LENGTH: 592
<212> TYPE: DNA
<213> ORGANISM: Trichoderma reesei
<220> FEATURE:
<223> OTHER INFORMATION: Strain IFO31328

<400> SEQUENCE: 16

```
tggagagcaa gttggactac atcaagggca tgggattcga tgccatctgg atcacacctg    60
ttgtgacgag tgagtctttt catacccttgc cctgccttgc ctcgcctcgc cttgcatgtg   120
tcgcatacag gcttctggta tgcatagcta aacctgatac ctctggacag acagtgatgg   180
gggctaccat ggctattggg cggaggacat cgactccatc aactctcatt atggctctgc   240
```

```
ggacgatctc aagagtctcg tcaacgccgc gcatagcaag gtattccctt ttgttcacac      300
cagacttcat gattatcaaa attaacacaa accagggctt ctatatgatg gtggacgtcg      360
tggccaacca catgggctac gccaatatct ctgacgatag tccctctcca ctgaaccagg      420
cctcgtcgta tcaccccgag tgtgatatcg actacaacaa ccaaaccagc gtcgagaact      480
gctggatcag cggcctcccg gatctcaaca cgcagagctc aaccatccgc agcctctacc      540
aggactgggt ctccaacctc gtgtccacgt acggcttcga cggcgtccgc at             592
```

<210> SEQ ID NO 17
<211> LENGTH: 592
<212> TYPE: DNA
<213> ORGANISM: Trichoderma reesei
<220> FEATURE:
<223> OTHER INFORMATION: Strain IFO31326

<400> SEQUENCE: 17

```
tggagagcaa gttggactac atcaagggca tgggattcga tgccatctgg atcacacctg       60
ttgtgacgag tgagtctttt cataccttgc cctgccttgc ctcgcctcgc cttgcatgtg      120
tcgcatacag gcttctggta tgcatagcta aacctgatac ctytggacag acagtgatgg      180
gggctaccat ggctattggg cggaggacat cgactccatc aactctcatt atggctctgc      240
ggacgatctc aagagtctcg tcaacgccgc gcatagcaag gtattccctt ttgttcacac      300
cagacttcat gattatcaaa attaacacaa accagggctt ctatatgatg gtggacgtcg      360
tggccaacca catgggctac gccaatatct ctgacgatag tccctctcca ctgaaccagg      420
cctcgtcgta tcaccccgag tgtgatatcg actacaacaa ccaaaccagc gtcgagaact      480
gctggatcag cggcctcccg gatctcaaca cgcagagctc aaccatccgc agcctctacc      540
aggactgggt ctccaacctc gtgtccacgt acggcttcga cggcgtccgc at             592
```

<210> SEQ ID NO 18
<211> LENGTH: 583
<212> TYPE: DNA
<213> ORGANISM: Trichoderma koningii
<220> FEATURE:
<223> OTHER INFORMATION: Strain IAM12534

<400> SEQUENCE: 18

```
tggagagcaa gttggactac atcaagggca tgggattcga tgccatctgg atcacgcctg       60
ttgtgacgag tgagtctttg ccctgtcccg ccttgcctcg ggtcgtacat gggctgctag      120
agtgaacagc tgcactgat acctctgaac agacagtgat gggggctacc atggctattg      180
ggcggaggat ctcgattcca tcaactctca ctacggctct gcggatgact tgaagagtct      240
cgtcaacgcc gcacatagca aggtacttct tcctggcatg atatgacctt cgcctattct      300
cctggttcta acgcgagaca aaccagggct tctatatgat ggtagacgtc gtggccaacc      360
acatgggcta cgccaacatc tccgatgaca gccctccccc tctgaaccag gcctcttcgt      420
atcacgccga gtgtgacatt gactacaaca accagaccag cgtccagaac tgctggatca      480
gcggcctccc tgatctcgac acgcagagcc cgaccatccg cagcctctac caggactggg      540
tctccaacct cgtgtccacg tacggcttcg acggcgtccg cat                        583
```

<210> SEQ ID NO 19
<211> LENGTH: 584
<212> TYPE: DNA
<213> ORGANISM: Trichoderma viride
<220> FEATURE:

<223> OTHER INFORMATION: Strain SAM1427

<400> SEQUENCE: 19

```
tggagagcaa gttggactac atcaagggca tgggatttga tgccatctgg atcactcctg      60
ttgtgacgag tgagtttcac cttgccttgc cttgcgtcgc acaaagcctt cgagagggaa     120
taggtagctg actctgtgat acccatgggt agacagtgat ggcggctatc atggctactg     180
ggcggaggac attgactcca tcaattccca ttatggctct gcagacgact tgaagagtct     240
tgtcaatgcc gcgcatagca aggtattttc ttcccagcat tggtttgatg tttgcccctt     300
tggcattatt ctcaagcaag aaaccagggc ttctatatga tggtggatgt cgtcgccaac     360
catatgggct acgccaacat caccgacgat agtcctactc ctctgaacca agcctcttcg     420
tatcacccgg agtgtgacat cgactacagc aaccagacca gcgtccagga atgctggatc     480
agcggcctcc cggatctcga caccgagagc ccgacgatcc gcagcctcta ccaggactgg     540
gtctccaatc tcgtgtccac gtacggcttc gacggcgtcc gcat                     584
```

<210> SEQ ID NO 20
<211> LENGTH: 614
<212> TYPE: DNA
<213> ORGANISM: Trichoderma ghanense
<220> FEATURE:
<223> OTHER INFORMATION: Strain IAM13109

<400> SEQUENCE: 20

```
tggagagcaa gttggactac atcaagggca tgggattcga tgccatctgg atcacccctg      60
ttgtgacgag tgagtctttt gccttgcctt gccttgcctt gccttgcctt gccttgcctt     120
rccttgcctt gtgtcgcaca caggctcctg aggaaatggc ctgatgctga taccttggaa     180
tagacagtga tgggggttat catggctatt gggcggagga cattgattcc atcaactctc     240
attacggctc tgcggacgac ctgaagagtc tcgtcaatgc cgcgcatagc aaggtacatc     300
tccccatcat tgacataggt ttacccttt gcatgattct gacgtgagac aaaccagggc     360
ttctatatga tggtggacgt cgtggccaac cacatgggct acgccaacat ctccgacgac     420
agtccttctc ctctgaacca agcgtcgtcc tatcacccag agtgtgacat tgactacaac     480
aaccagacca gcgtccagaa ctgctggatc agcggcctcc cggatctcaa cacgcagagc     540
tcgacgatcc gcagcctcta ccagggctgg gtctccgacc tcgtgtccac ctacggcttc     600
gacggcgtcc gcat                                                      614
```

<210> SEQ ID NO 21
<211> LENGTH: 572
<212> TYPE: DNA
<213> ORGANISM: Trichoderma saturnisporum
<220> FEATURE:
<223> OTHER INFORMATION: Strain IAM12535
<220> FEATURE:
<221> NAME/KEY: modified_base
<222> LOCATION: (445)..(445)
<223> OTHER INFORMATION: a, c, t, g, unknown or other

<400> SEQUENCE: 21

```
tggagagcaa gctggactac atcaagggca tgggattcga tgccatctgg atcacgcctg      60
ttgtgacgag tgagtctttg attaccttgt gtcgcacaca gtcttataga ggagatggat     120
cacactgaca tgtccggata gacagtcagg ggggctacca wggctactgg gcagaggaca     180
ttgactccat caattctcat tacgctctg cggacgacct gaagagtctc gtcaatgccg     240
cgcatagcaa ggtacttctt cctctcattg acatgccttt attcctttcg cgttgtccta     300
```

```
aaccgagatt tacagggctt ctatatgatg gtggatgtcg tcgccaacca catgggcaac    360
gccaacatct ccgacgatag tcctcctcct ctgaacgaag cctcttcgta tcaccccag    420 tgtgacattg actacaacaa ccamnccagc gtccagaact gctggatcag cggcctcccg    480
gatctcaaca cccagagctc gacgatccgc agcctctacc aggactgggt ccacaacctc    540
gtgtcgacgt acggcttcga cggcgtccgc at                                 572
```

<210> SEQ ID NO 22
<211> LENGTH: 572
<212> TYPE: DNA
<213> ORGANISM: Trichoderma polysporum
<220> FEATURE:
<223> OTHER INFORMATION: Strain SAM357

<400> SEQUENCE: 22

```
tggagggcaa gttggattac atcaagggga tgggatttga tgctatttgg atcacgcctg    60
ttgtaacgag taagttattc ataacagcct cagatatcat ctcctgggtc aatagctaat    120
atatcttgat agatagcgat caggggtatc atggctactg ggcagaggat ctcgattcta    180
tcaattctca ctatggttct tcggatgatt tgaagagtct tgtcgatgct gcacacagca    240
aggtacgtca tatcacctca cccccctaca ttctgctaat cctcatggat cgtgctaaac    300
cgaatgttaa aatagggctt ctatatgatg gtcgatgttg ttgccaatca catgggatat    360
gcaaacatca ccgacgacct tcccactcct ctaaaccaaa actcgtctta ccacgcagag    420
tgtaacatcg actataacaa tcagaccagc gtcgaaaact gctggatcga tggtctccca    480
gaccttgaca cacagagcga gactatccgc acccttaca aggactgggt ttccaacctc    540
gtctccacat acggcttcga cggcgtccgc at                                 572
```

<210> SEQ ID NO 23
<211> LENGTH: 571
<212> TYPE: DNA
<213> ORGANISM: Trichoderma reesei
<220> FEATURE:
<223> OTHER INFORMATION: Strain IFO31329

<400> SEQUENCE: 23

```
tggagggcaa gttggactac atcaagggca tgggattcga cgccatctgg atcacgcccg    60
tcgttacgag tgagttacac acagcctcag gcattacctc ttgaatgcgc ttctaatgtt    120
aatatttaaa tagatagcga cggggggtac cacggttact gggctgagtc tctggattcg    180
atcaattctc attatggttc tgcggatgat ttaaagagtc tcgttgatgc tgcgcatagc    240
aaggtacgtg atactccaca ccccatctta tatgcctcta ttttcgaagt acggtgctaa    300
aaaggtgaaa acagggtttc tatatgatgg tagatgttgt tgccaatcat atgggttatg    360
ccaacatttc tgacgacctc ccaactcccc tgaacgaaaa ctcgtcgtat catccagaat    420
gcgacattga ctacaacaac cagaccagcg tcgaaaactg ctggatcgat ggccttccgg    480
atctcgacac tcagagccct accatccgca gcctctacca ggactgggtc tccaacctcg    540
tatcgaccta cggcttcgac ggcgtccgca t                                  571
```

<210> SEQ ID NO 24
<211> LENGTH: 572
<212> TYPE: DNA
<213> ORGANISM: Trichoderma hamatum
<220> FEATURE:
<223> OTHER INFORMATION: Strain IAM12505

<400> SEQUENCE: 24

```
tggagagcaa gttggactat atcaagggca tgggatttga cgccatctgg atcacgcccg      60
tcgttacgag tgagttatat acagcctcac acattatccc ttcaaagagc atctaatatt     120
tatatttaaa tagacagtga taagggctat cacggctact gggcagaaga tatcgattct     180
attaattctc actatggttc tgcggacgat ttaaagagtc tcgtcgatgc tgcgcatagc     240
aaggtacatc atacgcaaca ccccatctta tatgcctcta ctctcgaaat gtcctgctaa     300
aacaagtgaa acagggctt ctacatgatg gtagatgttg tcgccaatca tatgggctat      360
gccaatattc ctgacgacct tccaaccccc ctgaacgaga actcgtcgta tcacccggaa     420
tgcgacattg actacaacaa cgagaccagc gtcgaaaact gctggatcag cggtctcccc     480
gatctcgaca cccagagccc taccatccgc agtctctacc aggactgggt ctccaacctc     540
gtctcgacct acggcttcga cggcgtccgc at                                    572
```

<210> SEQ ID NO 25
<211> LENGTH: 1329
<212> TYPE: DNA
<213> ORGANISM: Trichoderma viride
<220> FEATURE:
<223> OTHER INFORMATION: Strain IAM5141

<400> SEQUENCE: 25

```
gccgacacgg cagactggag gtctcgtacc atctactttg ccctgacaga ccgaattgct      60
cgcagctcaa gcgacacggg aggctctgcg tgtacaaatc tgaatgacta ctgtggtggc     120
acgttccagg gcttggagag caagctggac tacatcaagg gcatgggatt tgatgccatc     180
tggatcaacc ccgtcgtaac caacagtgat ttcggcttcc atggctactg ggcactggat     240
ctaaacacta tcaattctca ctatggcact gcggatgatt taaagagtct cgttgatgct     300
gcacatggca agggcttcta catgatggtc gacgttgtag ccaaccacat gggaaacgca     360
aacatcacag acgactcccc ctcccctctg aaccaacaat cctcatacca cacaaaatgt     420
gacattgact caacaaacca gaccagcgtc gaaaactgtt ggcttgctgg cctcccagac     480
gttgacaccc aggaccctac catcaggagc ctctaccagg actgggtgtc caacctggta     540
tctacatacg gcttcgacgg cgtccgcatc gacaccgtca ggcacgtcga gcaggactac     600
tggcccggct tcgtcaatgc cagcggcgtg tactgcatcg gcgaagtctt caacggagac     660
ccagacttta tgcagcccta ccaatcgctc atgcccggcc tcctcaacta cgccatcttc     720
tacccctca cgccttttta tcagcagacg ggctcctccc aagccctggt cgacatgcat     780
gaccgtctca gtcgttccc agacccgacg gcgctgggca cctttgtcga taaccacgac     840
aaccccgct tcctcagcgt caagaacgac acgtctctct tcaagaatgc cctgacctac     900
accattctcg gccgaggcat ccccattgtc tactacggct ccgagcaagc cttttcggga     960
agcaacgacc ccgccaacag agaggacctc tggcgcagcg gctacaacac cgagacggac    1020
atgtacaatg ccatctccaa gctcaccttt gccaagcaca cggccggcgg cctcgccgac    1080
aacgaccaca agcacctgta cgtcgagccc acggcatacg cctggagccg cgccggcggc    1140
aagctggtgg cctttaccac caacagcggc ggcggcagct cggcccagtt ctgcttcggc    1200
acgcaggtcc ccaacgggag ctggacgaat gtgtttgatg gcggcaatgg cccgacgtac    1260
actgctgatg gcaatggaca gctctgcttg accacgacga atggtgagcc gattgtgctg    1320
ctgtcttca                                                            1329
```

<210> SEQ ID NO 26
<211> LENGTH: 443
<212> TYPE: PRT
<213> ORGANISM: Trichoderma viride
<220> FEATURE:
<223> OTHER INFORMATION: Strain IAM5141

<400> SEQUENCE: 26

```
Ala Asp Thr Ala Asp Trp Arg Ser Arg Thr Ile Tyr Phe Ala Leu Thr
1               5                   10                  15

Asp Arg Ile Ala Arg Ser Ser Asp Thr Gly Gly Ser Ala Cys Thr
            20                  25                  30

Asn Leu Asn Asp Tyr Cys Gly Gly Thr Phe Gln Gly Leu Glu Ser Lys
        35                  40                  45

Leu Asp Tyr Ile Lys Gly Met Gly Phe Asp Ala Ile Trp Ile Asn Pro
    50                  55                  60

Val Val Thr Asn Ser Asp Phe Gly Phe His Gly Tyr Trp Ala Leu Asp
65                  70                  75                  80

Leu Asn Thr Ile Asn Ser His Tyr Gly Thr Ala Asp Asp Leu Lys Ser
                85                  90                  95

Leu Val Asp Ala Ala His Gly Lys Gly Phe Tyr Met Met Val Asp Val
            100                 105                 110

Val Ala Asn His Met Gly Asn Ala Asn Ile Thr Asp Asp Ser Pro Ser
        115                 120                 125

Pro Leu Asn Gln Gln Ser Ser Tyr His Thr Lys Cys Asp Ile Asp Phe
    130                 135                 140

Asn Asn Gln Thr Ser Val Glu Asn Cys Trp Leu Ala Gly Leu Pro Asp
145                 150                 155                 160

Val Asp Thr Gln Asp Pro Thr Ile Arg Ser Leu Tyr Gln Asp Trp Val
                165                 170                 175

Ser Asn Leu Val Ser Thr Tyr Gly Phe Asp Gly Val Arg Ile Asp Thr
            180                 185                 190

Val Arg His Val Glu Gln Asp Tyr Trp Pro Gly Phe Val Asn Ala Ser
        195                 200                 205

Gly Val Tyr Cys Ile Gly Glu Val Phe Asn Gly Asp Pro Asp Phe Met
    210                 215                 220

Gln Pro Tyr Gln Ser Leu Met Pro Gly Leu Leu Asn Tyr Ala Ile Phe
225                 230                 235                 240

Tyr Pro Leu Asn Ala Phe Tyr Gln Gln Thr Gly Ser Ser Gln Ala Leu
                245                 250                 255

Val Asp Met His Asp Arg Leu Ser Ser Phe Pro Asp Pro Thr Ala Leu
            260                 265                 270

Gly Thr Phe Val Asp Asn His Asp Asn Pro Arg Phe Leu Ser Val Lys
        275                 280                 285

Asn Asp Thr Ser Leu Phe Lys Asn Ala Leu Thr Tyr Thr Ile Leu Gly
    290                 295                 300

Arg Gly Ile Pro Ile Val Tyr Tyr Gly Ser Glu Gln Ala Phe Ser Gly
305                 310                 315                 320

Ser Asn Asp Pro Ala Asn Arg Glu Asp Leu Trp Arg Ser Gly Tyr Asn
                325                 330                 335

Thr Glu Thr Asp Met Tyr Asn Ala Ile Ser Lys Leu Thr Phe Ala Lys
            340                 345                 350

His Thr Ala Gly Gly Leu Ala Asp Asn Asp His Lys His Leu Tyr Val
        355                 360                 365

Glu Pro Thr Ala Tyr Ala Trp Ser Arg Ala Gly Gly Lys Leu Val Ala
```

```
                    370                 375                 380
Phe Thr Thr Asn Ser Gly Gly Ser Ser Ala Gln Phe Cys Phe Gly
385                 390                 395                 400

Thr Gln Val Pro Asn Gly Ser Trp Thr Asn Val Phe Asp Gly Gly
                405                 410                 415

Gly Pro Thr Tyr Thr Ala Asp Gly Asn Gly Gln Leu Cys Leu Thr Thr
                420                 425                 430

Thr Asn Gly Glu Pro Ile Val Leu Leu Ser Ser
                435                 440
```

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctcgagtta gtggtggtgg tggtggtgtg aagacagcag caa                43

<210> SEQ ID NO 28
<211> LENGTH: 462
<212> TYPE: PRT
<213> ORGANISM: Aspergillus nidulans

<400> SEQUENCE: 28

```
Met Lys Leu Ala Ser Thr Leu Ala Gly Leu Leu Pro Leu Ile Ser
1               5                   10                  15

Thr Val Ser Ala Ala Asp Val Asp Ala Trp Lys Ser Arg Asn Ile Tyr
                20                  25                  30

Phe Ala Leu Thr Asp Arg Val Ala Arg Gly Ser Asp Asp Thr Gly Gly
                35                  40                  45

Asp Ala Cys Asp Asp Leu Ser Thr Tyr Cys Gly Gly Thr Phe Lys Gly
        50                  55                  60

Leu Glu Gly Lys Leu Asp Tyr Ile Lys Gly Met Gly Phe Asp Ala Ile
65                  70                  75                  80

Trp Ile Thr Pro Val Val Ala Asn His Asp Gly Gly Tyr His Gly Tyr
                85                  90                  95

Trp Ala Lys Asp Leu Tyr Ser Ile Asn Glu Asn Tyr Gly Thr Ala Asp
                100                 105                 110

Asp Leu Lys Ser Leu Val Ser Ala Ala His Glu Lys Gly Ile Tyr Ile
            115                 120                 125

Met Ala Asp Val Val Ala Asn His Met Gly Ser Pro Ile Ser Asp Asn
        130                 135                 140

Gln Pro Glu Ser Leu Ser Gln Glu Ser Ala Tyr His Ser Ala Cys Thr
145                 150                 155                 160

Ile Asp Tyr Ser Ser Gln Glu Ser Ile Glu Thr Cys Arg Ile Ala Asp
                165                 170                 175

Asp Leu Pro Asp Val Asn Thr Glu Ser Glu Glu Ile Arg Thr Leu Phe
                180                 185                 190

Lys Glu Trp Ile Thr Trp Leu Val Lys Glu Tyr Glu Phe Asp Gly Leu
            195                 200                 205

Arg Ile Asp Thr Val Lys His Val Glu Lys Asp Phe Trp Ser Asp Phe
        210                 215                 220

Ser Ser Ala Ala Gly Val Tyr Thr Ile Gly Glu Val Phe Asp Gly Asp
225                 230                 235                 240
```

```
Pro Asp Tyr Leu Ala Gly Tyr Ala Asn Thr Met Asp Gly Leu Leu Asn
                245                 250                 255

Tyr Ala Val Tyr Pro Val Asn Asn Phe Tyr Gln Gln Ala Gly Ser
            260                 265                 270

Ala Gln Asp Ile Val Asp Met His Asp Lys Ile Asp Ser Ser Phe Pro
            275                 280                 285

Asp Pro Ser Ala Leu Gly Thr Phe Ile Asp Asn His Asp Asn Ala Arg
            290                 295                 300

Trp Leu Ser Asn Lys Asp Asp Lys Ser Leu Leu Lys Asn Ala Leu Ala
305                 310                 315                 320

Tyr Val Ile Leu Ala Arg Gly Ile Pro Ile Val Tyr Tyr Gly Thr Glu
                325                 330                 335

Gln Gly Tyr Ala Gly Gly Asn Asp Pro Glu Asn Arg Glu Asp Leu Trp
            340                 345                 350

Arg Ser Asn Phe Asp Thr Asp Ala Asp Leu Tyr Lys Ala Ile Ser Leu
            355                 360                 365

Leu Ser Ala Ala Arg Ser Ala Ala Gly Gly Leu Gly Asp Asn Asp His
            370                 375                 380

Val His Leu His Val Ala Glu Ser Ala Tyr Ala Trp Ser Arg Ala Glu
385                 390                 395                 400

Gly Lys Leu Val Val Val Thr Ser Asn Ser Gly Ser Gly Ser Glu Asn
                405                 410                 415

Glu Ile Cys Phe Asp Ser Lys Thr Pro Asn Gly Ser Trp Glu Asn Ile
            420                 425                 430

Phe Gly Glu Gly Thr Ile Ser Ala Asp Asp Ser Gly Gln Ile Cys Val
            435                 440                 445

Ser Ile Thr Asn Gly Glu Pro Ala Val Leu Val Ala Gln Ser
            450                 455                 460

<210> SEQ ID NO 29
<211> LENGTH: 460
<212> TYPE: PRT
<213> ORGANISM: Gibberella zeae

<400> SEQUENCE: 29

Met Lys Leu Leu Gln Leu Ala Ala Leu Val Ala Ser Ile Ser Pro Phe
1               5                   10                  15

Ala Ser Ala Ala Asp Ala Asn Ala Trp Lys Ser Arg Asn Ile Tyr Phe
            20                  25                  30

Ala Leu Thr Asp Arg Val Ala Arg Ser Asp Ser Asp Ser Gly Gly Asn
            35                  40                  45

Ala Cys Ser Asn Leu Gly Asn Tyr Cys Gly Gly Thr Phe Lys Gly Leu
            50                  55                  60

Glu Ala Lys Leu Asp Tyr Ile Lys Gly Met Gly Phe Asp Ala Ile Trp
65              70                  75                  80

Ile Thr Pro Val Val Glu Asn Thr Asp Gly Gly Tyr His Gly Tyr Trp
                85                  90                  95

Ala Lys Asp Leu Tyr Glu Val Asn Ala Lys Tyr Gly Thr Lys Asp Asp
            100                 105                 110

Leu Lys Ser Leu Val Lys Thr Ala His Ser Lys Asn Ile Tyr Val Met
            115                 120                 125

Ala Asp Val Val Ala Asn His Met Gly Lys Gly Ile Gln Asp His Arg
            130                 135                 140

Pro Glu Pro Leu Asn Gln Gln Ser Ser Tyr His Ser Pro Cys Ala Ile
```

```
                145                 150                 155                 160
Asp Tyr Asn Asn Gln Asn Ser Ile Glu Gln Cys Glu Ile Ala Asp Leu
                165                 170                 175

Pro Asp Leu Asn Thr Gly Ser Glu Thr Val Lys Lys Val Leu Asn Asp
            180                 185                 190

Trp Ile Ser Trp Leu Val Thr Glu Tyr Ser Phe Asp Gly Ile Arg Ile
        195                 200                 205

Asp Thr Val Lys His Val Glu Lys Ser Phe Trp Pro Asp Phe Gln Lys
    210                 215                 220

Ala Ala Gly Val Tyr Ala Ile Gly Glu Val Trp Asp Gly Ser Pro Asp
225                 230                 235                 240

Tyr Leu Ala Gly Tyr Ser Lys Val Met Pro Gly Leu Leu Asn Tyr Ala
                245                 250                 255

Ile Tyr Tyr Pro Met Asn Arg Phe Tyr Gln Gln Lys Gly Asp Pro Ser
            260                 265                 270

Ala Val Val Asp Met Tyr Asn Glu Ile Ser Gln Lys Phe Asp Asp Pro
        275                 280                 285

Thr Val Leu Gly Thr Phe Ile Asp Asn His Asp Asn Pro Arg Trp Leu
    290                 295                 300

Ser Gln Lys Asn Asp Lys Ala Leu Leu Lys Asn Ala Leu Ala Tyr Val
305                 310                 315                 320

Ile Leu Ser Arg Gly Ile Pro Ile Val Tyr Tyr Gly Thr Glu Gln Gly
                325                 330                 335

Tyr Ala Gly Gly Asn Asp Pro Ala Asn Arg Glu Asp Leu Trp Arg Ser
            340                 345                 350

Ser Phe Lys Thr Asp Ser Asp Leu Tyr Gln Thr Ile Ser Lys Leu Gly
        355                 360                 365

Lys Ala Arg Ser Ala Val Gly Gly Leu Ala Gly Asn Asp Gln Lys Phe
    370                 375                 380

Leu Lys Ser Asn Asp Ser Ala Leu Ile Trp Ser Arg Ala Asn Asn Asp
385                 390                 395                 400

Leu Ile Val Val Thr Met Asn Arg Gly Gln Gly Phe Ser Gly Gln Tyr
                405                 410                 415

Cys Phe Asn Thr Gly Ala Asn Asn Lys Thr Trp Glu Arg Val Leu Gly
            420                 425                 430

Gln Gly Thr Val Lys Ser Asp Gly Ser Gly Gln Leu Cys Val Ser Tyr
        435                 440                 445

Thr Asn Gly Glu Pro Glu Val Leu Val Ala Ala Asn
    450                 455                 460

<210> SEQ ID NO 30
<211> LENGTH: 600
<212> TYPE: PRT
<213> ORGANISM: Magnaporthe grisea

<400> SEQUENCE: 30

Met Phe Phe Phe Lys Val Leu Val Ala Phe Leu Leu Gln Ile Val Thr
1               5                   10                  15

Val Tyr Ala Ala Asp Thr Ala Ala Trp Lys Ser Arg Ser Ile Tyr Phe
            20                  25                  30

Ala Leu Thr Asp Arg Val Ala Arg Gly Ser Asn Asp Thr Gly Gly Ala
        35                  40                  45

Ser Cys Gly Asn Leu Ser Lys Tyr Cys Gly Gly Thr Phe Lys Gly Leu
    50                  55                  60
```

```
Glu Ser Lys Leu Asp Tyr Ile Lys Asn Leu Gly Phe Asp Ser Ile Trp
 65                  70                  75                  80

Ile Asn Pro Val Val Ser Asn Lys Ala Asp Gly Tyr His Gly Tyr Trp
                 85                  90                  95

Ala Gln Asp Leu Tyr Ala Ile Asn Ser Asn Tyr Gly Ser Ala Ala Asp
            100                 105                 110

Leu Lys Ser Leu Val Asn Thr Ala His Ser Lys Gly Ile Tyr Val Met
        115                 120                 125

Val Asp Val Val Ala Asn His Met Gly Pro Gly Ser Ile Ser Asp Asn
    130                 135                 140

Arg Pro Ala Pro Leu Asn Gln Asn Ser Ser Tyr His Ser Gln Cys Thr
145                 150                 155                 160

Ile Asp Asn Ser Asn Gln Ser Ser Val Glu Asn Cys Trp Val Ala Asn
                165                 170                 175

Leu Pro Asp Ile Asn Thr Gln Ser Ser Gly Ile Arg Gln Leu Leu Asn
            180                 185                 190

Thr Trp Val Ser Trp Leu Val Lys Glu Tyr Ser Phe Asp Gly Val Arg
        195                 200                 205

Ile Asp Thr Val Lys His Val Glu Lys Ser Phe Trp Pro Gly Phe Val
    210                 215                 220

Lys Ser Ile Gly Ala Tyr Ala Ile Gly Glu Val Phe Asp Gly Asn Pro
225                 230                 235                 240

Ser Phe Met Ala Gly Tyr Ala Asn Leu Met Pro Gly Leu Leu Asn Tyr
                245                 250                 255

Ala Val Tyr Tyr Pro Met Asn Arg Phe Tyr Gln Gln Gly Asn Ser Pro
            260                 265                 270

Gln Glu Leu Val Asn Met Ile Asp Asn Ile Thr Ala Ser Phe Pro Asp
        275                 280                 285

Pro Ala Ala Leu Gly Thr Phe Leu Asp Asn His Asp Asn Pro Arg Trp
    290                 295                 300

Leu Asn Gln Thr Asn Asp Gln Thr Leu Leu Gln Asn Ala Leu Ala Phe
305                 310                 315                 320

Val Phe Leu Ser Arg Gly Ile Pro Ile Leu Tyr Tyr Gly Thr Glu Gln
                325                 330                 335

Gly Leu Val Gly Gly Asp Asp Pro Ala Asn Arg Glu Asp Leu Trp Arg
            340                 345                 350

Ser Gly Tyr Lys Thr Asp Thr Thr Leu His Gly Ala Val Ala Lys Leu
        355                 360                 365

Asn Ala Ala Arg Lys Ala Ala Gly Gly Leu Asp Gly Asn Asp His Thr
    370                 375                 380

His Leu Tyr Val Thr Asn Asp Thr Tyr Ala Trp Ser Arg Ala Gly Ala
385                 390                 395                 400

Asp Leu Val Val Leu Thr Thr Asn Ala Gly Arg Cys Ser His Ala Gln
                405                 410                 415

His Cys Phe Asn Thr Thr Arg Ala Asn Gly Arg Trp Ala Asp Val Tyr
            420                 425                 430

Gly Ser Gly Ala Tyr Val Phe Ser Asp Lys Thr Gly Arg Ala Cys Val
        435                 440                 445

Lys Leu Ala Asn Gly Gln Pro Val Val Leu Leu Leu Ala Asn Ser
    450                 455                 460

Thr Thr Gly Asp Gly Lys Pro Pro Thr Leu Pro Ala Pro Ile Thr Trp
465                 470                 475                 480

Tyr Asn Ser Thr Ser Pro Pro Asp Asp Ser Ala Asn Gly Ser Asn Val
```

```
            485                 490                 495
Cys Pro Pro Ala Val Ala Val Ser Phe Thr Val Arg Val Ala Thr Ala
            500                 505                 510

Pro Gly Asp Thr Ile Lys Met Val Gly Asn Thr Ala Gln Leu Gly Ser
            515                 520                 525

Trp Asp Ala Ala Lys Ala Pro Ser Leu Ser Ala Ser Gly Tyr Asn Ser
            530                 535                 540

Thr Asn Met Ala Trp Ser Ile Thr Leu Pro Met Ala Pro Gly Arg Thr
545                 550                 555                 560

Val Gln Tyr Lys Phe Val Lys Val Ser Arg Ser Gly Gly Thr Thr Trp
                565                 570                 575

Glu Ser Asp Pro Asn Arg Phe Tyr Thr Pro Pro Val Ser Gln Ala Thr
                580                 585                 590

Ala Asp Val Ser Asn Ile Trp Arg
                595                 600

<210> SEQ ID NO 31
<211> LENGTH: 661
<212> TYPE: PRT
<213> ORGANISM: Magnaporthe grisea

<400> SEQUENCE: 31

Met Ala Asn Lys Ile Leu Val Ala Tyr Ile Phe Ala Asp Phe Leu Phe
1               5                   10                  15

Val Leu Met Gly Ala Leu Met Leu Gly Phe Ser Ile Val Val Gly Asn
                20                  25                  30

Val Arg Asp Glu Val Pro Thr Glu Gly Asn Gln Ala Ala Arg Asn Leu
            35                  40                  45

Leu Tyr Gln Lys Phe Pro Leu Thr Ala Gly Ile Val Asn Ala Ile Phe
        50                  55                  60

Ile Phe Ile Thr Phe Leu Leu Thr Ile Pro Ala Leu Ser Thr Pro Ala
65                  70                  75                  80

Arg Gly Trp Leu Lys Met Ser Gly Tyr Leu Val Val Asn Ala Leu
                85                  90                  95

Phe Ser Leu Val Ile Gly Leu Phe Leu Trp Ile Met Thr Leu Lys Thr
                100                 105                 110

Arg Asp Asp Leu Phe Pro Ile Trp Val Gln Gln Thr Pro Gln Val Gln
            115                 120                 125

Ser Leu Met Glu Val Ser Phe Lys Cys Cys Gly Tyr Tyr Asn Ser Thr
        130                 135                 140

Ala Pro Ala Phe Val Thr Asn Gln Val Cys Pro Ser Pro Ala Ala Ser
145                 150                 155                 160

Ala Leu Met Arg Gly Cys Ala Thr Pro Ile Thr Ser Phe Ala Asn Val
                165                 170                 175

Phe Val Asp Asn Ile Phe Thr Gly Val Phe Gly Met Cys Gly Ile Asp
                180                 185                 190

Gly Leu Leu Val Ile Ala Thr Ala Cys Leu Leu Lys Asp Arg Lys Glu
            195                 200                 205

Gln Glu Arg Phe Arg His Ile Asp Gln Lys Thr Gly Pro Met Ser Thr
        210                 215                 220

Leu Pro Gly Gln Thr Ser Val Val Arg Gln Ala Asp Arg Ile Ala Arg
225                 230                 235                 240

Asn Glu Ser Asp Ser Gly Gly Asn Ser Cys Ser Asp Leu Gly Gln Tyr
                245                 250                 255
```

```
Cys Gly Gly Thr Phe Lys Gly Leu Gln Ser Lys Leu Asp Tyr Ile Arg
                260                 265                 270

Gly Met Gly Phe Asp Ala Ile Trp Ile Ser Pro Val Val Glu Asn His
            275                 280                 285

Lys Gly Gly Tyr His Gly Tyr Trp Ala Lys Asp Leu Tyr Ala Ile Asn
        290                 295                 300

Ser Lys Tyr Gly Thr Ala Asp Asp Leu Lys Ser Leu Ile Lys Ala Ala
305                 310                 315                 320

His Asp Lys Gly Phe Leu Leu Met Val Asp Val Val Ala Asn His Met
                325                 330                 335

Gly Asn Gly Pro Ile Ser Glu Asn Lys Pro Ala Pro Leu Asn Gln Glu
            340                 345                 350

Ser Ser Tyr His Pro Glu Cys Lys Ile Asp Tyr Ser Asn Gln Gln Ser
        355                 360                 365

Val Glu Arg Cys Arg Leu Gly Asn Leu Pro Asp Leu Asn Thr Glu Asp
                370                 375                 380

Pro Lys Ile Arg Thr Leu Leu Thr Asp Trp Ile Lys Trp Ile Val Ser
385                 390                 395                 400

Glu Phe Lys Val Asp Gly Leu Arg Ile Asp Thr Val Lys His Val Glu
                405                 410                 415

Lys Gly Phe Trp Pro Gly Phe Ala Trp Ala Ser Gly Val Tyr Thr Leu
            420                 425                 430

Gly Glu Val Tyr Ser Glu Asp Val Asp Tyr Leu Ala Gly Tyr Asp Lys
                435                 440                 445

Thr Met Gly Gly Phe Phe Asn Phe Pro Val Tyr Lys Ser Leu Gly Arg
450                 455                 460

Tyr Leu Gln Gln Gly Gln Ser Pro Gln Gly Leu Val Asp Asn His Asp
465                 470                 475                 480

Lys Ile Thr Arg Lys Phe Ser Asp Pro Thr Thr Leu Ala Asn Phe Leu
                485                 490                 495

Asp Ser His Asp Asp Pro Arg Trp Leu Ser Lys Asn Arg Asp Ala Ala
            500                 505                 510

Leu Leu Lys Asn Ala Leu Ala Tyr Val Leu Leu Ala Arg Gly Ile Pro
        515                 520                 525

Val Val Tyr Tyr Gly Thr Glu Gln Gly Phe Ser Gly Gly Ala Asp Pro
530                 535                 540

Trp Asn Arg Glu Asp Leu Trp Arg Ala Arg Tyr Arg Thr Asp Gly Asp
545                 550                 555                 560

Leu Tyr Arg Ala Ile Ser Arg Leu Ser Gly Val Arg Ala Gly Ala Gly
                565                 570                 575

Gly Leu Pro Ala Asp Asp Gln Ile His Leu Leu Val Asn Lys Asn Ser
            580                 585                 590

Tyr Ala Phe Ser Arg Asp Gly Gly Val Val Leu Thr Thr Asn
        595                 600                 605

Arg Gly Ser Gly Phe Asn Gly Gln Glu Cys Phe Asp Thr Arg Gly Val
            610                 615                 620

Thr Ala Thr Trp Glu Asp Lys Phe Gly Ser Gly Thr Tyr Thr Ser Asp
625                 630                 635                 640

Glu Ser Gly Lys Val Cys Val Gln Val Lys Asn Gly Glu Pro Val Val
                645                 650                 655

Leu Val Arg Lys Lys
            660
```

<210> SEQ ID NO 32
<211> LENGTH: 463
<212> TYPE: PRT
<213> ORGANISM: Trichoderma viride
<220> FEATURE:
<223> OTHER INFORMATION: Strain IAM5141

<400> SEQUENCE: 32

```
Met Lys Leu Arg Ser Ala Val Pro Leu Leu Gln Leu Ser Leu Pro
1               5                   10                  15

Ala Val Leu Gly Ala Asp Thr Ala Asp Trp Arg Ser Arg Thr Ile Tyr
            20                  25                  30

Phe Ala Leu Thr Asp Arg Ile Ala Arg Ser Ser Ser Asp Thr Gly Gly
            35                  40                  45

Ser Ala Cys Thr Asn Leu Asn Asp Tyr Cys Gly Gly Thr Phe Gln Gly
50                  55                  60

Leu Glu Ser Lys Leu Asp Tyr Ile Lys Gly Met Gly Phe Asp Ala Ile
65                  70                  75                  80

Trp Ile Asn Pro Val Val Thr Asn Ser Asp Phe Gly Phe His Gly Tyr
                85                  90                  95

Trp Ala Leu Asp Leu Asn Thr Ile Asn Ser His Tyr Gly Thr Ala Asp
            100                 105                 110

Asp Leu Lys Ser Leu Val Asp Ala Ala His Gly Lys Gly Phe Tyr Met
            115                 120                 125

Met Val Asp Val Val Ala Asn His Met Gly Asn Ala Asn Ile Thr Asp
130                 135                 140

Asp Ser Pro Ser Pro Leu Asn Gln Gln Ser Ser Tyr His Thr Lys Cys
145                 150                 155                 160

Asp Ile Asp Phe Asn Asn Gln Thr Ser Val Glu Asn Cys Trp Leu Ala
                165                 170                 175

Gly Leu Pro Asp Val Asp Thr Gln Asp Pro Thr Ile Arg Ser Leu Tyr
            180                 185                 190

Gln Asp Trp Val Ser Asn Leu Val Ser Thr Tyr Gly Phe Asp Gly Val
            195                 200                 205

Arg Ile Asp Thr Val Arg His Val Glu Gln Asp Tyr Trp Pro Gly Phe
210                 215                 220

Val Asn Ala Ser Gly Val Tyr Cys Ile Gly Glu Val Phe Asn Gly Asp
225                 230                 235                 240

Pro Asp Phe Met Gln Pro Tyr Gln Ser Leu Met Pro Gly Leu Leu Asn
                245                 250                 255

Tyr Ala Ile Phe Tyr Pro Leu Asn Ala Phe Tyr Gln Gln Thr Gly Ser
            260                 265                 270

Ser Gln Ala Leu Val Asp Met His Asp Arg Leu Ser Ser Phe Pro Asp
            275                 280                 285

Pro Thr Ala Leu Gly Thr Phe Val Asp Asn His Asp Asn Pro Arg Phe
290                 295                 300

Leu Ser Val Lys Asn Asp Thr Ser Leu Phe Lys Asn Ala Leu Thr Tyr
305                 310                 315                 320

Thr Ile Leu Gly Arg Gly Ile Pro Ile Val Tyr Tyr Gly Ser Glu Gln
                325                 330                 335

Ala Phe Ser Gly Ser Asn Asp Pro Ala Asn Arg Glu Asp Leu Trp Arg
            340                 345                 350

Ser Gly Tyr Asn Thr Glu Thr Asp Met Tyr Asn Ala Ile Ser Lys Leu
            355                 360                 365

Thr Phe Ala Lys His Thr Ala Gly Gly Leu Ala Asp Asn Asp His Lys
```

```
                370                 375                 380
His Leu Tyr Val Glu Pro Thr Ala Tyr Ala Trp Ser Arg Ala Gly Gly
385                 390                 395                 400

Lys Leu Val Ala Phe Thr Thr Asn Ser Gly Gly Ser Ser Ala Gln
                405                 410                 415

Phe Cys Phe Gly Thr Gln Val Pro Asn Gly Ser Trp Thr Asn Val Phe
                420                 425                 430

Asp Gly Gly Asn Gly Pro Thr Tyr Thr Ala Asp Gly Asn Gly Gln Leu
                435                 440                 445

Cys Leu Thr Thr Thr Asn Gly Glu Pro Ile Val Leu Leu Ser Ser
                450                 455                 460

<210> SEQ ID NO 33
<211> LENGTH: 499
<212> TYPE: PRT
<213> ORGANISM: Aspergillus oryzae

<400> SEQUENCE: 33

Met Met Val Ala Trp Trp Ser Leu Phe Leu Tyr Gly Leu Gln Val Ala
1               5                   10                  15

Ala Pro Ala Leu Ala Ala Thr Pro Ala Asp Trp Arg Ser Gln Ser Ile
                20                  25                  30

Tyr Phe Leu Leu Thr Asp Arg Phe Ala Arg Thr Asp Gly Ser Thr Thr
                35                  40                  45

Ala Thr Cys Asn Thr Ala Asp Gln Lys Tyr Cys Gly Gly Thr Trp Gln
            50                  55                  60

Gly Ile Ile Asp Lys Leu Asp Tyr Ile Gln Gly Met Gly Phe Thr Ala
65              70                  75                  80

Ile Trp Ile Thr Pro Val Thr Ala Gln Leu Pro Gln Thr Thr Ala Tyr
                85                  90                  95

Gly Asp Ala Tyr His Gly Tyr Trp Gln Gln Asp Ile Tyr Ser Leu Asn
                100                 105                 110

Glu Asn Tyr Gly Thr Ala Asp Asp Leu Lys Ala Leu Ser Ser Ala Leu
            115                 120                 125

His Glu Arg Gly Met Tyr Leu Met Val Asp Val Ala Asn His Met
130                 135                 140

Gly Tyr Asp Gly Ala Gly Ser Ser Val Asp Tyr Ser Val Phe Lys Pro
145                 150                 155                 160

Phe Ser Ser Gln Asp Tyr Phe His Pro Phe Cys Phe Ile Gln Asn Tyr
                165                 170                 175

Glu Asp Gln Thr Gln Val Glu Tyr Cys Trp Leu Gly Asp Asn Thr Val
            180                 185                 190

Ser Leu Leu Asp Leu Asp Thr Thr Lys Asp Val Val Lys Asn Glu Trp
                195                 200                 205

Tyr Asp Trp Val Gly Ser Leu Val Ser Asn Tyr Ser Ile Asp Gly Leu
                210                 215                 220

Arg Ile Asp Thr Val Lys His Val Gln Lys Asp Phe Trp Pro Gly Tyr
225                 230                 235                 240

Asn Lys Ala Ala Gly Val Tyr Cys Ile Gly Glu Val Leu Asp Val Asp
                245                 250                 255

Pro Ala Tyr Thr Cys Pro Tyr Gln Asn Val Met Asp Gly Val Leu Asn
            260                 265                 270

Tyr Pro Ile Tyr Tyr Pro Leu Leu Asn Ala Phe Lys Ser Thr Ser Gly
                275                 280                 285
```

```
Ser Met Asp Asp Leu Tyr Asn Met Ile Asn Thr Val Lys Ser Asp Cys
    290                 295                 300

Pro Asp Ser Thr Leu Leu Gly Thr Phe Val Glu Asn His Asp Asn Pro
305             310                 315                 320

Arg Phe Ala Ser Tyr Thr Asn Asp Ile Ala Leu Ala Lys Asn Val Ala
                325                 330                 335

Ala Phe Ile Ile Leu Asn Asp Gly Ile Pro Ile Ile Tyr Ala Gly Gln
                340                 345                 350

Glu Gln His Tyr Ala Gly Gly Asn Asp Pro Ala Asn Arg Glu Ala Thr
            355                 360                 365

Trp Leu Ser Gly Tyr Pro Thr Asp Ser Glu Leu Tyr Lys Leu Ile Ala
    370                 375                 380

Ser Ala Asn Ala Ile Arg Asn Tyr Ala Ile Ser Lys Asp Thr Gly Phe
385             390                 395                 400

Val Thr Tyr Lys Asn Trp Pro Ile Tyr Lys Asp Asp Thr Thr Ile Ala
                405                 410                 415

Met Arg Lys Gly Thr Asp Gly Ser Gln Ile Val Thr Ile Leu Ser Asn
                420                 425                 430

Lys Gly Ala Ser Gly Asp Ser Tyr Thr Leu Ser Leu Ser Gly Ala Gly
                435                 440                 445

Tyr Thr Ala Gly Gln Gln Leu Thr Glu Val Ile Gly Cys Thr Thr Val
    450                 455                 460

Thr Val Gly Ser Asp Gly Asn Val Pro Val Pro Met Ala Gly Gly Leu
465             470                 475                 480

Pro Arg Val Leu Tyr Pro Thr Glu Lys Leu Ala Gly Ser Lys Ile Cys
                485                 490                 495

Ser Ser Ser
```